(12) United States Patent
Wang et al.

(10) Patent No.: US 12,067,725 B2
(45) Date of Patent: Aug. 20, 2024

(54) IMAGE REGION LOCALIZATION METHOD, IMAGE REGION LOCALIZATION APPARATUS, AND MEDICAL IMAGE PROCESSING DEVICE

(71) Applicant: Tencent Technology (Shenzhen) Company Limited, Shenzhen (CN)

(72) Inventors: Liang Wang, Shenzhen (CN); Jun Zhang, Shenzhen (CN)

(73) Assignee: TENCENT TECHNOLOGY (SHENZHEN) COMPANY LIMITED, Shenzhen (CN)

(*) Notice: Subject to any disclaimer, the term of this patent is extended or adjusted under 35 U.S.C. 154(b) by 576 days.

(21) Appl. No.: 17/222,471

(22) Filed: Apr. 5, 2021

(65) Prior Publication Data

US 2021/0225027 A1 Jul. 22, 2021

Related U.S. Application Data

(63) Continuation of application No. PCT/CN2020/077746, filed on Mar. 4, 2020.

(30) Foreign Application Priority Data

Mar. 8, 2019 (CN) .......................... 201910175745.4

(51) Int. Cl.
*A61B 5/055* (2006.01)
*G06F 18/25* (2023.01)
(Continued)

(52) U.S. Cl.
CPC ............... *G06T 7/11* (2017.01); *A61B 5/055* (2013.01); *G06F 18/253* (2023.01);
(Continued)

(58) Field of Classification Search
CPC . G06T 7/11; G06T 7/0014; G06T 7/33; G06T 7/73; G06T 2207/10088;
(Continued)

(56) References Cited

U.S. PATENT DOCUMENTS

2008/0292194 A1* 11/2008 Schmidt .................. G06T 7/143
382/131
2017/0213340 A1* 7/2017 Kuo ...................... G06T 7/0012
(Continued)

FOREIGN PATENT DOCUMENTS

CN 106909778 A 6/2017
CN 106960221 A 7/2017
(Continued)

OTHER PUBLICATIONS

Tencent Technology, WO, PCT/CN2020/077746, Jun. 2, 2020, 5 pgs.
(Continued)

*Primary Examiner* — Marcos L Torres
(74) *Attorney, Agent, or Firm* — Morgan, Lewis & Bockius LLP

(57) ABSTRACT

Embodiments of this application disclose methods, systems, and devices for image region localization and medical image processing. In one aspect, a method comprises acquiring three-dimensional images of a target body part of a patient. The three-dimensional images comprise a plurality of magnetic resonant imaging (MRI) modalities. The method comprises registering a first image set of a first modality with a second image set of a second modality. After the registering, image features of the three-dimensional images are extracted. The image features are fused to obtain fused features. The method also comprises determining voxel types corresponding to voxels in the three-dimensional images according to the fused features. The method also (Continued)

comprises selecting, from the three-dimensional images, target voxels having a preset voxel type, obtaining position information of the target voxels, and localizing a target region within the target body part based on the position information of the target voxels.

20 Claims, 9 Drawing Sheets

(51) Int. Cl.
| | |
|---|---|
| G06T 7/00 | (2017.01) |
| G06T 7/11 | (2017.01) |
| G06T 7/33 | (2017.01) |
| G06T 7/73 | (2017.01) |
| G06V 10/44 | (2022.01) |
| G06V 10/80 | (2022.01) |
| G06V 10/82 | (2022.01) |
| G06V 10/84 | (2022.01) |

(52) U.S. Cl.
CPC .............. *G06T 7/0014* (2013.01); *G06T 7/33* (2017.01); *G06T 7/73* (2017.01); *G06V 10/454* (2022.01); *G06V 10/806* (2022.01); *G06V 10/82* (2022.01); *G06V 10/85* (2022.01); *G06T 2207/10088* (2013.01); *G06T 2207/20081* (2013.01); *G06T 2207/20084* (2013.01); *G06T 2207/30004* (2013.01); *G06V 2201/03* (2022.01)

(58) Field of Classification Search
CPC . G06T 2207/20081; G06T 2207/20084; G06T 2207/30004; G06T 2207/30068; G06T 2207/30096; G06T 7/0012; G06T 7/174; A61B 5/055; G06F 18/253; G06F 18/295; G06V 10/454; G06V 10/806; G06V 10/82; G06V 10/85; G06V 2201/03; G01R 33/4838; G01R 33/56341; G01R 33/5635; G01R 33/4822; G01R 33/5608
See application file for complete search history.

(56) References Cited

U.S. PATENT DOCUMENTS

2018/0053334 A1\* 2/2018 Schneider ................ G06T 7/11
2019/0057778 A1 2/2019 Porter et al.

FOREIGN PATENT DOCUMENTS

| CN | 107945168 A | 4/2018 |
|---|---|---|
| CN | 108062753 A | 5/2018 |
| CN | 109035261 A | 12/2018 |
| CN | 109166157 A | 1/2019 |
| CN | 109377496 A | 2/2019 |
| CN | 109978838 A | 7/2019 |
| CN | 110458813 A | 11/2019 |

OTHER PUBLICATIONS

Tencent Technology, IPRP, PCT/CN2020/077746, Aug. 25, 2021, 6 pgs.
Tencent Technology, ISR, PCT/CN2020/077746, Jun. 2, 2020, 2 pgs.

\* cited by examiner

IMAGE REGION LOCALIZATION METHOD, IMAGE REGION LOCALIZATION APPARATUS, AND MEDICAL IMAGE PROCESSING DEVICE

CROSS REFERENCE TO RELATED APPLICATIONS

This application is a continuation application of PCT Patent Application No. PCT/CN2020/077746, entitled "IMAGE REGION POSITIONING METHOD AND APPARATUS AND MEDICAL IMAGE PROCESSING DEVICE" filed on Mar. 4, 2020, which claims priority to Chinese Patent Application No. 201910175745.4, entitled "IMAGE REGION LOCALIZATION METHOD, IMAGE REGION LOCALIZATION APPARATUS, AND MEDICAL IMAGE PROCESSING DEVICE", filed with the State Intellectual Property Office of the People's Republic of China on Mar. 8, 2019, all of which are incorporated herein by reference in their entirety.

FIELD OF THE TECHNOLOGY

This application relates to the field of image processing technologies, and in particular, to an image region localization technology.

BACKGROUND OF THE DISCLOSURE

In recent years, machine learning technology that focuses on deep learning has attracted people's attention. Semantic segmentation is a typical process in which machine learning is utilized for image localization, and it uses some raw data (for example, medical three-dimensional images) as inputs and converts the inputs into masks with highlighted regions of interest. A region of interest may be referred to as a target region, and the target region may be, for example, a breast tumor region, and the like.

Existing target region identification methods based on three-dimensional (3D) images suffer from problems such as inaccurate identification.

SUMMARY

Embodiments of this application provide an image region localization method, an image region localization apparatus, and a medical image processing device, which can improve the accuracy of target identification.

An embodiment of this application provides an image region localization method, comprising:
  acquiring a plurality of three-dimensional (e.g., 3D) images of a target body part of a patient, the plurality of 3D images comprising a plurality of magnetic resonant imaging (MRI) modalities, the plurality of three-dimensional images including a first three-dimensional image set of a first modality and a second three-dimensional image set of a second modality;
  registering the first three-dimensional image set with the second three-dimensional image set;
  after the registering, extracting image features of the plurality of 3D images;
  fusing the image features of the plurality of 3D images; in accordance with the fusing, obtaining fused features;
  determining voxel types corresponding to voxels in the 3D images according to the fused features;
  selecting, from the 3D images, target voxels having a preset voxel type;
  obtaining position information of the target voxels; and
  localizing a target region within the target body part based on the position information of the target voxels.

In some embodiments, determining voxel types corresponding to voxels in the 3D images according to the fused features further comprises:
  for each of the voxels in the three-dimensional images:
    determining a respective fused feature corresponding to the voxel;
    calculating a fused feature probability corresponding to the respective fused feature;
    calculating a probability that the voxel corresponds to a respective voxel type of the voxel types based on the calculated fused feature probability; and
    determining the voxel type to which the voxel corresponds based on the determined probability that the each voxel is of each voxel type.

In some embodiments, the fusing the image features of the plurality of 3D images further comprises:
  acquiring preset feature weights corresponding to the image features; and
  weighting the image features of the plurality of 3D images based on the preset feature weights.

In some embodiments, the weighting the image features of the plurality of 3D images based on the preset feature weights further comprises:
  based on the position information of the target voxels, determining a first plurality of image features corresponding to voxels at the same position in the plurality of 3D images;
  weighting the first plurality of image features with the preset feature weights to obtain a plurality of weighted image features; and
  accumulating the plurality of weighted image features to obtain fused features of the voxels.

In some embodiments, the localizing a target region based on the position information of the target voxels further comprises:
  selecting a target 3D image from the plurality of 3D images; and
  localizing the target region on the target 3D image based on the position information of the target voxels.

In some embodiments, the localizing the target region on the target 3D image based on the position information of the target voxels further comprises:
  determining corresponding voxels on the target 3D images based on the position information of the target voxels to obtain the corresponding voxel; and
  setting a voxel value of each of the corresponding voxels to a preset value to identify the target region.

In some embodiments, the localizing the target region on the target 3D image based on the position information of the target voxels further comprises:
  calculating a mean of the position information of all of the target voxels to obtain position information of a central point of the target region; and
  localizing the central point of the target region on the target 3D image based on the position information of the central point.

In some embodiments, the extracting image features of the plurality of 3D images further comprises:
  preprocessing the plurality of 3D images to obtain a plurality of preprocessed 3D images; and
  extracting image features of the plurality of preprocessed 3D images.

In some embodiments, the preprocessing the plurality of 3D images further comprises:

acquiring a reference coordinate system and original coordinate systems of the plurality of 3D images; and transforming the original coordinate systems of the plurality of 3D images into the reference coordinate system.

In some embodiments, the preprocessing the plurality of 3D images further comprises:

acquiring a reference voxel spacing and original voxel spacings of the plurality of 3D images; and transforming the original voxel spacings of the plurality of 3D images into the reference voxel spacing.

In some embodiments, the preprocessing the plurality of 3D images further comprises:

acquiring a reference dimension and original dimensions of the plurality of 3D images; and transforming the original dimensions of the plurality of 3D images into the reference dimension.

Some embodiments of this application further provide a computing device, e.g., an image region localization apparatus, that includes one or more processors and memory. The memory stores one or more program modules (e.g., programs). The program modules include instructions for execution by the one or more processors The one or more program modules include:

an acquiring module configured to acquire a plurality of 3D images of a target body part of a patient's body, the plurality of 3D images including a plurality of 3D images of different modalities (e.g., different MRI modalities);

an extracting module configured to extract image features of the plurality of 3D images;

a fusing module configured to fuse the image features of the plurality of 3D images to obtain fused features;

a classification module configured to determine voxel types corresponding to voxels in the 3D images according to the fused features;

a screening module configured to select, from the 3D images, target voxels of which the voxel type is a preset voxel type to obtain position information of the target voxels; and a localization module configured to localize a target region based on the position information of the target voxels.

An embodiment of this application further provides a medical image processing device, the medical image processing device including a medical image acquisition unit, a processor, and a memory, the medical image acquisition unit being configured to acquire a plurality of 3D images of a target part of a living organism (e.g., a target body part of a patient);

the memory being configured to store image data and a plurality of instructions; and the processor being configured to read the plurality of instructions stored in the memory to perform the operations of:

acquiring a plurality of 3D images of a target part, the plurality of 3D images including a plurality of 3D images of different modalities; extracting image features of the plurality of 3D images; fusing the image features of the plurality of 3D images to obtain fused features; determining voxel types corresponding to voxels in the 3D images according to the fused features; selecting, from the 3D images, target voxels of which the voxel type is a preset voxel type to obtain position information of the target voxels; and localizing a target region based on the position information of the target voxels.

In executing the operation of determining voxel types corresponding to voxels in the 3D images according to the fused features, the processor specifically performs the operations of: determining a fused feature corresponding to each of the voxels in the 3D images; calculating a probability that the fused feature corresponding to the each voxel is of each voxel type to obtain a probability that the each voxel is of each voxel type; and determining the voxel type corresponding to the each voxel according to the probability that the each voxel is of each voxel type.

In executing the operation of fusing the image features of the plurality of 3D images, the processor specifically performs the operations of: acquiring preset feature weights corresponding to the image features; and weighting the image features of the plurality of 3D images based on the preset feature weights;

In executing the operation of weighting the image features of the plurality of 3D images based on the preset feature weights, the processor specifically performs the operations of: determining a plurality of image features corresponding to voxels at the same position in the plurality of 3D images; weighting the plurality of image features with the preset feature weights to obtain a plurality of weighted image features; and accumulating the plurality of weighted image features to obtain the fused features of the voxels.

In executing the operation of localizing a target region based on the position information of the target voxels, the processor specifically performs the operations of: selecting a target 3D image from the plurality of 3D images; and localizing the target region on the target 3D image based on the position information of the target voxel.

An embodiment of this application provides an image region localization method, including:

acquiring a plurality of 3D images of a target part, the plurality of 3D images including a plurality of 3D images of different modalities;

extracting image features of the plurality of 3D images;

fusing the image features of the plurality of 3D images to obtain fused features;

determining voxel types corresponding to voxels in the 3D images according to the fused features;

selecting, from the 3D images, target voxels of which the voxel type is a breast tumor type to obtain position information of the target voxels; and localizing a breast tumor region based on the position information of the target voxels.

In some embodiments, the determining voxel types corresponding to voxels in the 3D images according to the fused features includes:

determining the fused feature corresponding to each of the voxels in the 3D images;

calculating a probability that the fused feature corresponding to the each voxel is of each voxel type to obtain a probability that the each voxel is of each voxel type; and determining the voxel type corresponding to the each voxel according to the probability that the each voxel is of each voxel type.

In some embodiments, the fusing the image features of the plurality of 3D images includes:

acquiring preset feature weights corresponding to the image features; and weighting the image features of the plurality of 3D images based on the preset feature weights.

In some embodiments, the weighting the image features of the plurality of 3D images based on the preset feature weights includes:
  determining a plurality of image features corresponding to voxels at the same position in the plurality of 3D images;
  weighting the plurality of image features with the preset feature weights to obtain a plurality of weighted image features; and
  accumulating the plurality of weighted image features to obtain fused features of the voxels.

In some embodiments, the localizing a breast tumor region based on the position information of the target voxel includes:
  selecting a target 3D image from the plurality of 3D images; and
  localizing the breast tumor region on the target 3D image based on the position information of the target voxels.

In some embodiments, the localizing the breast tumor region on the target 3D image based on the position information of the target voxel includes:
  determining corresponding voxels on the target 3D image based on the position information of the target voxels to obtain the corresponding voxels; and
  setting a voxel value of each of the corresponding voxels to a preset value to identify the breast tumor region.

In some embodiments, the localizing the breast tumor region on the target three-dimensional image based on the position information of the target voxel includes:
  calculating a mean of the position information of all of the target voxels to obtain position information of a central point of the breast tumor region; and
  localizing the central point of the breast tumor region on the target 3D image based on the position information of the central point.

In some embodiments, the extracting image features of the plurality of 3D images includes:
  preprocessing the plurality of 3D images to obtain a plurality of preprocessed 3D images; and
  extracting image features of the plurality of preprocessed 3D images.

In some embodiments, the preprocessing the plurality of 3D images includes:
  acquiring a reference coordinate system and original coordinate systems of the plurality of 3D images; and
  transforming the original coordinate systems of the plurality of 3D images into the reference coordinate system.

In some embodiments, the preprocessing the plurality of 3D images includes:
  acquiring a reference voxel spacing and original voxel spacings of the plurality of 3D images; and
  transforming the original voxel spacings of the plurality of 3D images into the reference voxel spacing.

In some embodiments, the preprocessing the plurality of 3D images includes:
  acquiring a reference dimension and original dimensions of the plurality of 3D images; and
  transforming the original dimensions of the plurality of 3D images into the reference dimension.

An embodiment of this application further provides an image region localization apparatus, including:
  an acquiring module configured to acquire a plurality of 3D images of a target part, the plurality of 3D images including a plurality of 3D images of different modalities;
  an extracting module configured to extract image features of the plurality of 3D images;
  a fusing module configured to fuse the image features of the plurality of 3D images to obtain fused features;
  a classification module configured to determine voxel types corresponding to voxels in the 3D images according to the fused features;
  a screening module configured to select, from the 3D images, target voxels of which the voxel type is a breast tumor type to obtain position information of the target voxels; and
  a localization module configured to localize a breast tumor region based on the position information of the target voxels.

An embodiment of this application further provides a medical image processing device, the medical image processing device
  including a medical image acquisition unit, a processor, and a memory,
  the medical image acquisition unit being configured to acquire a plurality of 3D images of a target part of a living organism (e.g., a target body part of a patient);
  the memory being configured to store image data and a plurality of instructions; and
  the processor being configured to read the plurality of instructions stored in the memory to perform the operations of:
  acquiring a plurality of 3D images of a target part, the plurality of 3D images including a plurality of 3D images of different modalities; extracting image features of the plurality of 3D images; fusing the image features of the plurality of 3D images to obtain fused features; determining voxel types corresponding to voxels in the 3D images according to the fused features; selecting, from the 3D images, target voxels of which the voxel type is a breast tumor type to obtain position information of the target voxels; and localizing a breast tumor region based on the position information of the target voxels.

In executing the operation of determining voxel types corresponding to voxels in the 3D images according to the fused features, the processor specifically performs the operations of: determining a fused feature corresponding to each of the voxels in the 3D images; calculating a probability that the fused feature corresponding to the each voxel is of each voxel type to obtain a probability that the each voxel is of each voxel type; and
  determining the voxel type corresponding to the each voxel according to the probability that the each voxel is of each voxel type.

In executing the operation of fusing the image features of the plurality of 3D images, the processor specifically performs the operations of: acquiring preset feature weights corresponding to the image features; and weighting the image features of the plurality of 3D images based on the preset feature weights;

In executing the operation of weighting the image features of the plurality of 3D images based on the preset feature weights, the processor specifically performs the operations of: determining a plurality of image features corresponding to voxels at the same position in the plurality of 3D images; weighting the plurality of image features with the preset feature weights to obtain a plurality of weighted image features; and accumulating the plurality of weighted image features to obtain fused features of the voxels.

In executing the operation of localizing a breast tumor region based on the position information of the target voxels, the processor specifically performs the operations of: selecting a target 3D image from the plurality of 3D images; and localizing the breast tumor region on the target 3D image based on the position information of the target voxel.

According to the embodiments of this application, a plurality of 3D images of a target part (e.g., a target body part of a patient) can be acquired, where the plurality of 3D images include a plurality of 3D images of different modalities; and it is possible to: extract image features of the plurality of 3D images; fuse the image features of the plurality of 3D images to obtain fused features; determine voxel types corresponding to voxels in the 3D images according to the fused features; select, from the 3D images, target voxels of which the voxel type is a preset voxel type to obtain position information of the target voxels; and localize a target region based on the position information of the target voxels.

In the embodiments of this application, the fused feature can be obtained based on different image features provided by the 3D images of different modalities, and the target region can be directly localized according to the fused features. Due to the plurality of 3D images of different modalities, the subsequent region localizing operation may be caused to be analyzed and processed from a plurality of angles, which can reduce the probability of a false determination, thus improving a localizing accuracy for the target region.

In another aspect, some embodiments of this application provide a computing device (e.g., computer device or computer system) with one or more processors and memory. The memory stores one or more programs for execution by the one or more processors. The one or more programs comprise instructions that, when executed by the one or more processors, cause the one or more processors to perform any of the methods disclosed herein.

In another aspect, some embodiments of this application provide a non-transitory computer-readable storage medium. The non-transitory computer-readable storage medium stores instructions that, when executed by one or more processors of a computing device or a computer system, cause the computing device or the computer system to perform any of the methods disclosed herein.

BRIEF DESCRIPTION OF THE DRAWINGS

To describe the technical solutions in embodiments of this application more clearly, the following briefly describes accompanying drawings required for describing the embodiments. Apparently, the accompanying drawings in the following description show merely some embodiments of this application, and a person skilled in the art may still derive other drawings from these accompanying drawings without creative efforts.

DESCRIPTION OF EMBODIMENTS

The technical solutions in the embodiments disclosed in this application are clearly and completely described in the following with reference to the accompanying drawings in the embodiments of this application. Apparently, the embodiments to be described are merely some embodiments of this application rather than all of the embodiments. All other embodiments obtained by a person skilled in the art based on the embodiments of this application without creative efforts shall fall within the protection scope of this application.

Embodiments of this application provide an image region localization method, an image region localization apparatus, and a medical image processing device.

The image region localization apparatus may be specifically integrated in an electronic device which may include a magnetic resonance imaging device, a medical image data processing device, a medical image data storage device, and the like.

Figure 1A:
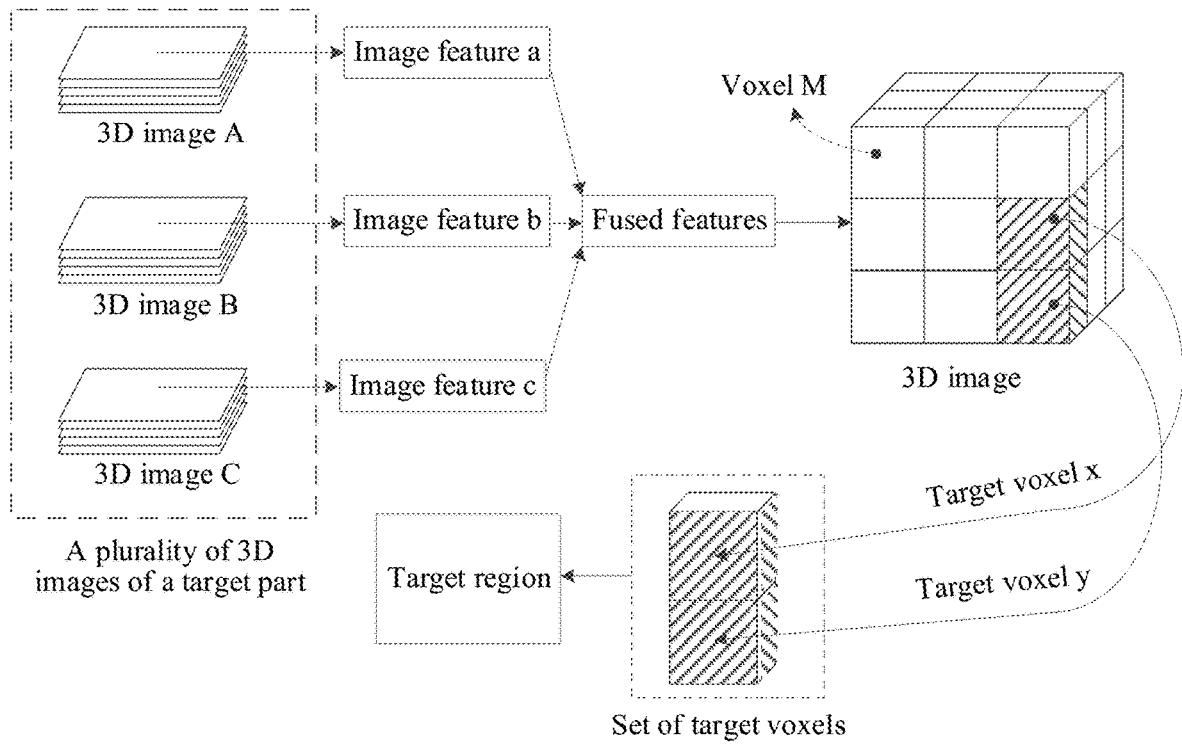
FIG. 1a is a schematic diagram of a scenario of an image region localization method according to some embodiments of this application.

FIG. 1a is a schematic diagram of a scenario of an image region localization method according to some embodiments of this application. Referring to FIG. 1a, an electronic device may: acquire a plurality of 3D images of a target part, the plurality of 3D images including a plurality of 3D images of different modalities, for example, a 3D image A, a 3D image B, and a 3D image C in FIG. 1a; extract image features of the plurality of 3D images to respectively obtain an image feature a, an image feature b, and an image feature c; fuse the image features of the plurality of 3D images to obtain fused features; determine voxel types corresponding to voxels in the 3D images according to the fused features; select, from the 3D images, target voxels of which the voxel type is a preset voxel type to obtain position information of the target voxels; and localize a target region based on the position information of the target voxels.

Detailed descriptions are separately made below. Sequence numbers of the following embodiments are not intended to limit preference orders of the embodiments.

In the embodiment of this application, description is to be given with regard to the image region localization apparatus. The image region localization apparatus may be specifically integrated in an electronic device which may include a magnetic resonance image acquisition device, a magnetic resonance imaging device, a medical image data processing device, a medical image data storage device, and the like.

Figure 1B:
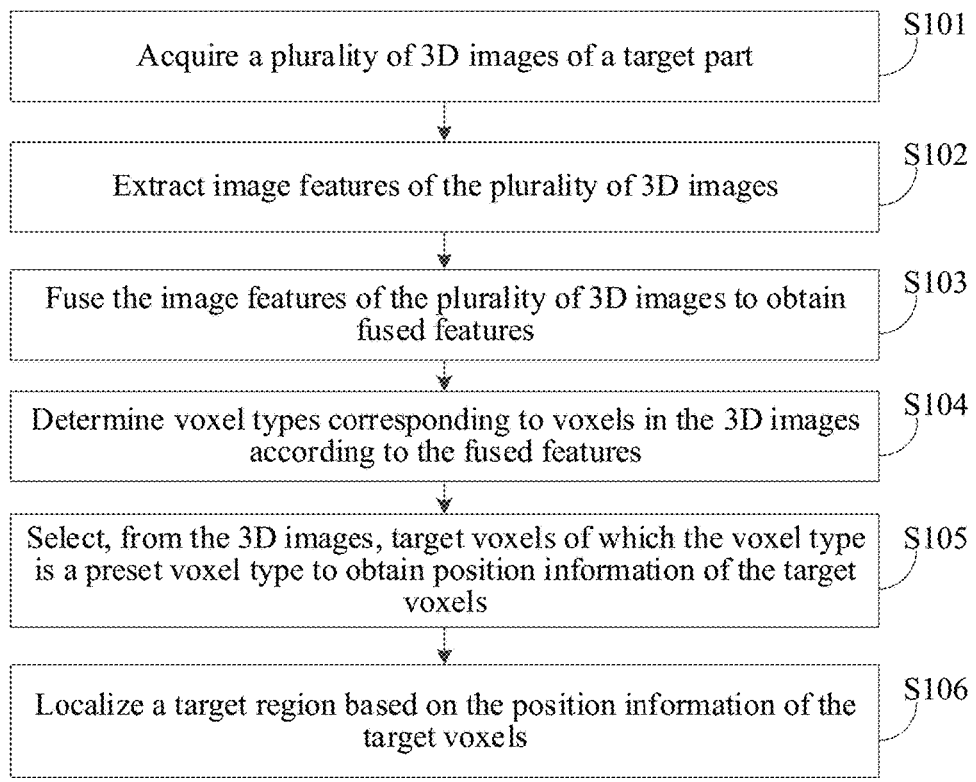
FIG. 1b is a schematic flowchart of the image region localization method according to some embodiments of this application.

In this embodiment, an image region localization method is provided. As shown in FIG. 1b, the image region localization method may include the following specific steps.

S101: Acquire a plurality of 3D images of a target part.

The target part may be a constituent part of a body of a living organism such as an animal or a plant (e.g., a human, a cat, and a dog, and the like), or a constituent part of a non-living organism, such as a human tissue section, an animal specimen, and a metabolite of a living organism. The target part may further include a portion of a 3D model in computer vision, for example, a part of a ribcage of a patient, a brain of a dog specimen, and the like.

The 3D images may be 3D images each having three dimensions including a length, a width, and a height, or may be continuous two-dimensional images each having three dimensions including a length, a width, and a time. The 3D images may be, for example, laser holograms, computer 3D models, 3D magnetic resonance images, and the like.

The plurality of 3D images of the target part may be acquired in various methods. In some embodiments, a plurality of to-be-processed 3D images may be acquired from locally stored images or externally stored images. For example, the 3D images may be acquired from a local image database. Alternatively, the 3D images may be acquired through communications with other storage devices via a network.

In some embodiments, the electronic device may also acquire the 3D images by itself and select the plurality of to-be-processed 3D images therefrom.

In some embodiments, in order to facilitate selection of the target part by a user and improvement of the accuracy of identification, the acquired 3D image of a modality of a part may be displayed on the electronic device. The user may preview the displayed image and intercept the target part on the preview interface, so as to reduce an influence in time and accuracy of information about a non-target region on subsequent image processing, thereby improving efficiency and accuracy of identifying the target region.

By acquiring the plurality of 3D images of different modalities of the target part, the subsequent region localizing operation may be caused to be analyzed and processed from a plurality of angles, thus improving accuracy of identification.

In some embodiments, the 3D image may be a 3D magnetic resonance image, that is, the method may be used for performing region localizing on the 3D magnetic resonance image. In this case, a device for acquiring the 3D magnetic resonance image may be a magnetic resonance image acquisition device.

Specifically, a magnetic resonance imaging technology is to use the principle of nuclear magnetic resonance (NMR), and according to different attenuation of the released energy in different structural environments within a substance, to detect an emitted electromagnetic wave by adding a gradient magnetic field, so that a position and a type of an atomic nucleus forming an object may be learned, thereby drawing an image of the internal structure of the object.

The magnetic resonance signals acquired by the magnetic resonance imaging device may be subjected to a series of post-processing to generate image sequences of different modalities such as T1 Weighted and T2 Weighted, angiography (Magnetic Resonance Angiography, MRA), and diffusion weighted image (DWI), apparent diffusion coefficient (ADC), fat suppression (FS) images, and dynamic contrast-enhanced (DCE) imaging. The image sequences can generate 3D MRI images with various characteristics, which can not only reflect anatomic forms of a human body in 3D space, but also reflect information about physiological functions such as human blood flow and cell metabolism.

At present, MRI is widely used in medical diagnosis, and has good resolution of soft tissues such as bladder, rectum, uterus, vagina, joints, and muscles. In addition, various parameters for MRI may be used for imaging, and MRI images of different modalities can provide rich diagnostic information. Moreover, a required profile may be freely selected by adjusting the magnetic field, and 3D image sequences can be generated from various directions. In addition, due to no ionizing radiation damage to the human body, MRI is often used in detection and diagnosis of diseases such as tumors in the reproductive system, breast cancer. For example, an MRI of the pelvis can help find problems such as tumors in the ovaries, uterus, prostate, rectum, and anus.

In this case, the target part is intercepted on the preview interface, so as to reduce an influence in time and accuracy information about no pathology (information about a non-target region) on subsequent image processing, thereby improving efficiency and accuracy of identifying pathological tissues.

A 3D magnetic resonance image sequence is a cube formed by stacking a plurality of two-dimensional magnetic resonance images.

The magnetic resonance image acquisition device may apply a radio frequency pulse of a specific frequency to a to-be-detected target in a static magnetic field, so that a hydrogen proton inside the to-be-detected target is excited to cause magnetic resonance. After the pulse is stopped, the proton generates a nuclear magnetic resonance signal during the relaxation process, and a magnetic resonance signal is generated through processing processes such as receiving, spatial encoding, and image reconstruction of the nuclear magnetic resonance signal, that is, the 3D magnetic resonance image sequence is obtained through acquisition.

For example, in some embodiments, a 3D magnetic resonance image may be acquired from a medical image data storage system. Alternatively, a 3D magnetic resonance image is acquired through communication with other storage devices through a network.

S102: Extract image features of the plurality of 3D images.

The image features may include a color feature, a texture feature, a shape feature, a spatial relationship feature, and the like of the image.

In this embodiment, dimensions of a length and a width of a two-dimensional neural network may be transformed into dimensions of a length, a width, and a height of a 3D neural network by adding a dimension of a height to a neural network. After 3D models trained by the 3D neural networks are obtained, a 3D image of each modality is inputted into a plurality of channels of the 3D model to extract image features. After a plurality of extraction operations, the image features of all the 3D images obtained in step S101 can be obtained.

At present, commonly used 3D image processing networks may include a 3D convolutional neural network (3D CNN), a 3D fully convolutional network (3D FCN), and the like.

In some embodiments, in order to solve the effect of convolution and pooling operations on image dimensions and improve calculation efficiency, a preset 3D FCN model may be adopted to extract image features of a 3D image, which is to be described in detail below.

The FCN may classify images at a voxel level, thereby solving the problem of semantic segmentation. Unlike the classic CNN that uses a plurality of fully-connected layers after the convolutional layer to map a feature map generated by the convolutional layer into an image feature with a fixed length for classification, the FCN may accept input images of any dimension, and adopt a deconvolution layer to up-sample the feature map of the last convolutional layer to restore the feature map to the same dimension as the input image, so that each voxel can be predicted, spatial information in the original input image is retained, and finally classification for each voxel is performed on the up-sampled feature map. Briefly, a difference between the FCN and the CNN is that the FCN replaces the fully-connected layer of CNN with a convolutional layer, so that the network output is no longer a category but a heatmap, and in order to solve the influence of convolution and pooling operations on the image dimensions, a method of up-sampling is provided for restoration.

However, compared with the convolution operation on the 2D image by the 2D FCN, the 3D FCN not only considers length information and width information of the image, but also considers height information of the image.

Figure 1C:
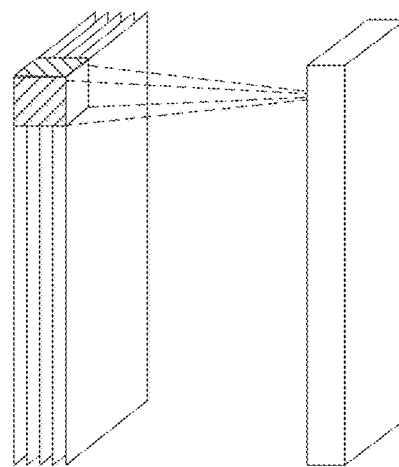
FIG. 1c is a process of performing convolution on a 3D image sequence by using a 3D convolutional kernel according to some embodiments of this application.

FIG. 1c is a process of using a 3D convolutional kernel to convolve a 3D image sequence in a 3D FCN. A height dimension of the convolution operation in the figure is N. Continuous N-frame images are stacked into a cube, and then the 3D convolutional kernel is adopted to perform a convolution operation on the cube. In the structure, each feature map in the convolutional layer is connected to a plurality of adjacent consecutive frames in the previous layer, so that height information can be captured. That is, through the convolution between the N frames of images, the 3D FCN extracts a correlation between the heights.

In a case that the 3D image is inputted into a preset 3D FCN, the inputted 3D image may pass through a plurality of convolutional layers and down-sampling layers to obtain a heat map, that is, a high-dimensional feature map, and then image features are obtained after the high-dimensional feature map passes a plurality of up-sampling layers.

Specifically, a 3D convolutional kernel with a size of 1×1×1 is allowed to complete sliding of one row in an axis y from low to high on an axis x on a 5×5×5 3D image sequence with a step size of 1, then complete sliding of an image in an axis z from bottom to top on the axis y, and finally complete sliding of the entire 3D image sequence on the axis z from low to high. Each stop position is taken into the 3D FCN network, and a category score of 5×5×5 positions can be obtained.

The preset 3D FCN model may be acquired from a locally stored model set or an externally stored model set. For example, a preset 3D FCN model may be acquired through communication with other storage devices through a network.

Since a 3D convolutional kernel provides only one weight, only one type of features can be extracted from the cube. Since the feature extraction obtained by one convolutional kernel is insufficient, a plurality of features may be identified by adding a plurality of convolutional kernels. A plurality of convolutional kernels are adopted, and each channel corresponds to a convolutional kernel, so that the 3D FCN can extract a plurality of features of a 3D image.

S103: The image features of the plurality of 3D images are fused to obtain fused features.

After the image features of the plurality of 3D images are acquired in step S102, the image features that reflect type information in the target part from a plurality of angles may be fused, and the obtained fused feature has accuracy and diversity.

At present, common fusion methods may include serial fusion, parallel fusion, selection fusion, transformation fusion, and the like.

Serial fusion is to combine all image features according to a serial method to form a new image feature, that is, complete the serial fusion of features.

However, parallel fusion is to combine all image features according to a parallel method to form a new image feature, that is, complete the serial fusion of features.

Selective fusion is to select one or more optimal data from each one-dimensional data corresponding to all image features, and finally combine all the selected data into new features, that is, complete the selective fusion of features.

Transformation fusion is to put all the image features together and transform the image features into a brand-new feature expression method by using certain mathematical methods, that is, complete the transformation fusion of features.

Figure 1D:
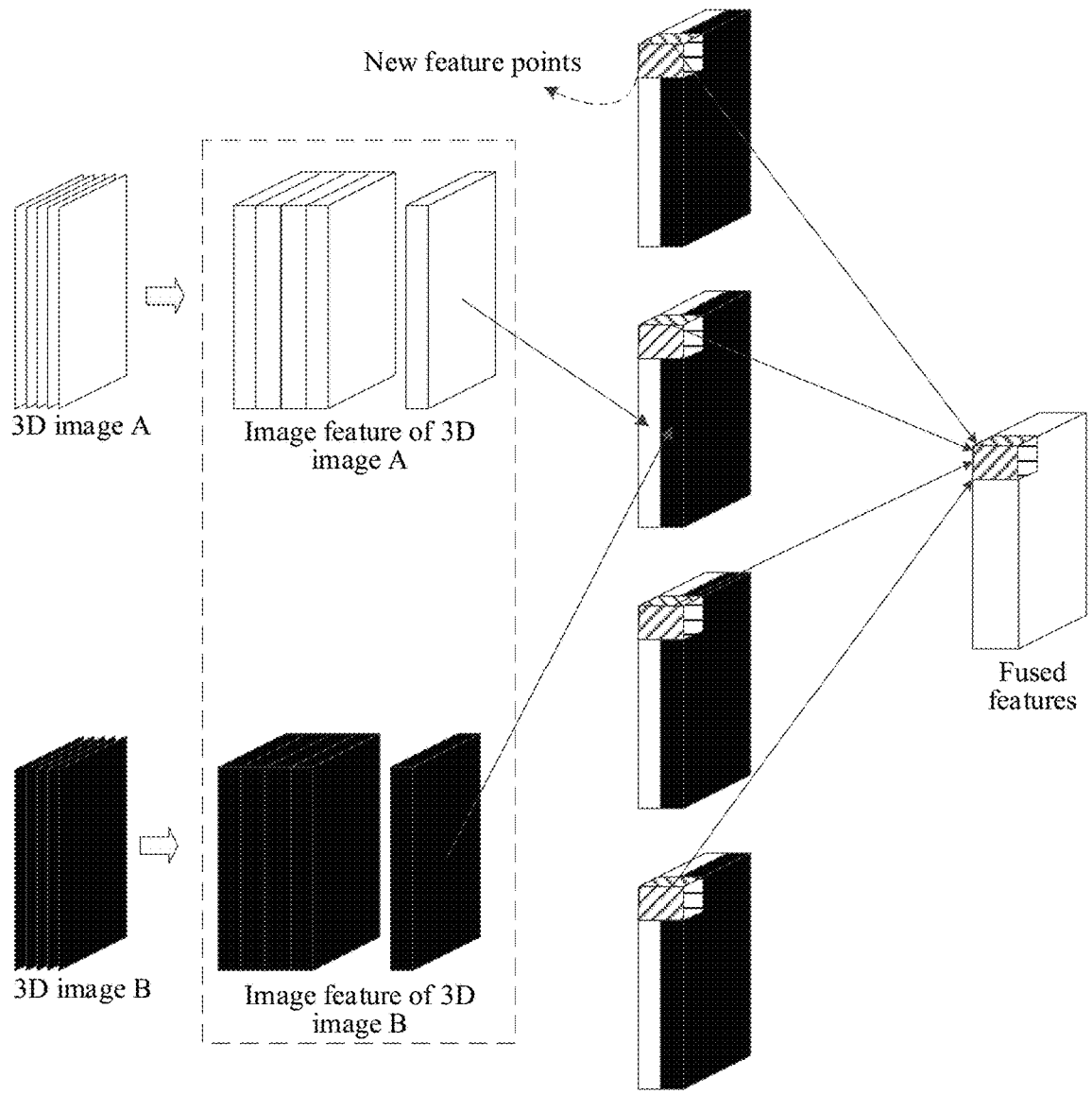
FIG. 1d is a schematic diagram of a feature fusion according to some embodiments of this application.

In some embodiments, FIG. 1d is a schematic diagram of feature fusion. As shown in the figure, after image features are extracted for a 3D image A and a 3D image B, feature points on the same layer and at the same position of the 3D image A and the 3D image B are serially fused to obtain new feature points. After repetitions a plurality of times, the fused features of the 3D image A and the 3D image B can be obtained.

Figure 1E:
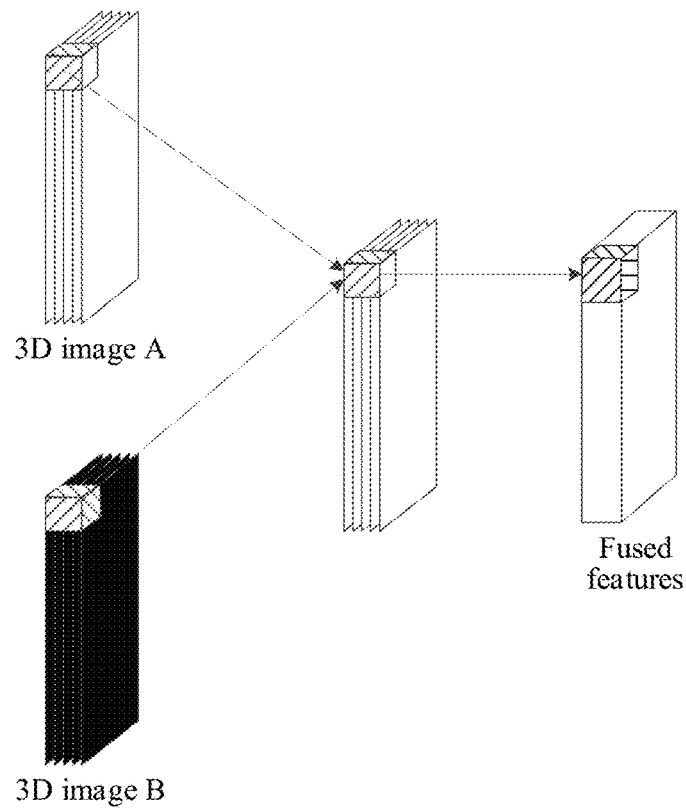
FIG. 1e is a schematic diagram of another feature fusion according to some embodiments of this application.

In some other embodiments, FIG. 1e is a schematic diagram of another feature fusion. As shown in the figure, in a case that image features of a plurality of 3D images are extracted in step S103, voxels on the same layer and at the same position of the 3D image A and the 3D image B are serially fused to obtain fused features of the voxel according to the fusion result.

S104: Determine voxel types corresponding to voxels in the 3D images according to the fused features.

After the fused features in step S103 are acquired, a probability that the fused feature corresponding to the each voxel is of each voxel type may be calculated according to the fused feature, thus determining the probability that the voxel corresponds to the voxel type in the 3D image.

Since different fused features have different value ranges, in order to reduce the influence of the value range of the fused feature on the final result, balance the value range of the fused feature, and improve the accuracy of identifying the target region, it is necessary to normalize the range of the fused feature in advance to normalize the values of the fused features to an interval of [0, 1].

Commonly used normalization methods may include function normalization, dimension normalization, sorting normalization, and the like.

The function normalization may be to map feature values to the interval of [0, 1] through a mapping function, such as using a maximum and minimum normalization method, which is linear mapping. In addition to this, the normalization operation may also be performed through the mapping of a non-linear function such as a log function.

The dimension normalization may also use the maximum and minimum normalization method, but the maximum and minimum values are the maximum and minimum values of the category, that is, local maximum and minimum values are used.

Sorting normalization may directly sort the features by size regardless of the original value range of features, and assign a new value to the feature according to the sorting corresponding to the feature.

After the probability that the voxel corresponds to the voxel type in the 3D image is determined through the fused features according to the above operations, the voxel type corresponding to the voxel may be determined according to the probability that each of the voxels is of each voxel type. For example, a dictionary may be adopted to query the voxel type corresponding to the probability, thus determining the voxel type corresponding to the voxel in the 3D image.

The dictionary may be acquired from a local internal memory or an external internal memory. For example, a dictionary may be acquired from a local database. Alternatively, a dictionary may be acquired through communication with other storage devices through a network.

The voxel type may refer to a type represented by the voxel. For example, the voxel type may include a pathological type, that is, classification of the disease represented by the voxel from the perspective of pathology, which focuses on description of a current symptom.

Table 1 is a schematic diagram of a dictionary format. As shown in the table, in some embodiments, it is determined, through the fused features, that the probability that the voxel type corresponding to the voxel in the 3D image are respectively 0, (0, x], (x, y), [y, 1), and 1. The voxel type corresponding to the probability 0 is A, the voxel type corresponding to the probability greater than 0 and less than or equal to x is B, the voxel type corresponding to the probability greater than x and less than y is C, and the voxel type corresponding to the probability greater than or equal to y and less than 1 is D.

TABLE 1

| Probability | 0 | (0, x] | (x, y) | [y, 1) |
|---|---|---|---|---|
| Voxel type | A | B | C | D |

In some embodiments, the fused features may be optimized by using a probabilistic graphical model (GPM) to obtain more detailed fused features, thus improving the accuracy of identifying target regions.

The GPM can explain a correlation (dependency) relationship between each voxel in the 3D image from a mathematical perspective, that is, the GPM may be used for determining the voxel type corresponding to the voxel in the 3D image.

A GPM is a generic term for a class of models based on probabilistic correlations expressed by graphical patterns. The GPM combines the knowledge of probability theory and graph theory, and uses graphs to represent a joint probability distribution of variables related to the model.

Commonly used GPMs include a maximum entropy Markov model (MEMM), a hidden Markov model (HMM), a conditional random field (CRF) algorithm, and the like.

A probability graph is composed of nodes (also referred to as vertices) and links (also referred to as edges or arcs) therebetween. In the GPM, each node represents one or a group of random variables, and the link represents a probability relationship between these variables. The GPM is mainly divided into two types. One type is a directed graphical model, that is, a Bayesian network. Such a graphical model is characterized by directional links. The other type is undirected graphical models, or Markov random fields. Links of such a model are undirected.

In some embodiments, after the GPM acquires the fused feature in step S103, the probability that the voxel corresponds to the voxel type in the 3D image may also be determined according to the fused features.

The Naïve Bayes (NB) model is a generative model in the classification problem, which is modelled by a joint probability $P(x,y)=P(x|y)P(y)$, and a posterior probability $P(y|x)$ is solved by using the Bayes' theorem. The NB assumes that eigenvectors of inputs x $(x(1), x(2), \ldots, x(j), \ldots, x(n))$ are conditional independence, that is:

$$P(x|y)P(y)=P(y)\Pi P(x(j)|y)$$

The HMM is a generative model used for labelling Y for sequence data X, and a joint probability $P(X, Y)$ is modelled by using a Markov chain:

$$P(X,Y)=\Pi P(yt|yt-1)P(xt|yt)$$

Then, a maximum value of $P(Y|X)P(Y|X)$ is solved by using a Viterbi algorithm.

A logistic regression (LR) analysis model is a discriminative model in the classification problem, which directly uses an LR function to model a conditional probability $P(y|x)P(y|x)$. In fact, a logistic regression function is a special form of a normalized exponential function (softmax), and LR is equivalent to the maximum entropy model, which may be written in the form of maximum entropy:

$$Pw(y|x)=\exp(\Sigma iwifi(x,y))/Zw(x)$$

$Zw(x)$ is a normalization factor, w is a parameter preset by a model, and $ifi(x, y)$ is a feature function, which can describe a relationship of (x, y).

The CRF is a discriminative model to solve the labelling problem. Each voxel i has a category label xi and a corresponding observation value yi, each voxel is used as a node, and the relationship between a voxel and a voxel is used as an edge, which constitutes a conditional random field. The category label xi corresponding to the voxel i may be inferred by observing the variable yi.

The conditional random field conforms to the Gibbs distribution, where y is the observed value:

$$P(Y=y|I)=\exp(-E(y|I))/Z(I)$$

E(y|I) is an energy function:

$$E(x)=\Sigma i\Psi u(yi)+\Sigma(i<j)\Psi p(yi,yj)$$

A unary potential function $\Sigma i\Psi u(yi)$ is an output from a front-end 3D convolutional neural network. A binary potential function is as follows:

$$\Psi p(yi,yj)=u(yi,yj)\Sigma M\omega(m)k(m)G(fi,fj)$$

The binary potential function is used for describing the relationship between voxels. The same label is allowed to be allocated to similar voxels, while different labels are allocated to voxels differing greatly from each other.

Figure 1F:
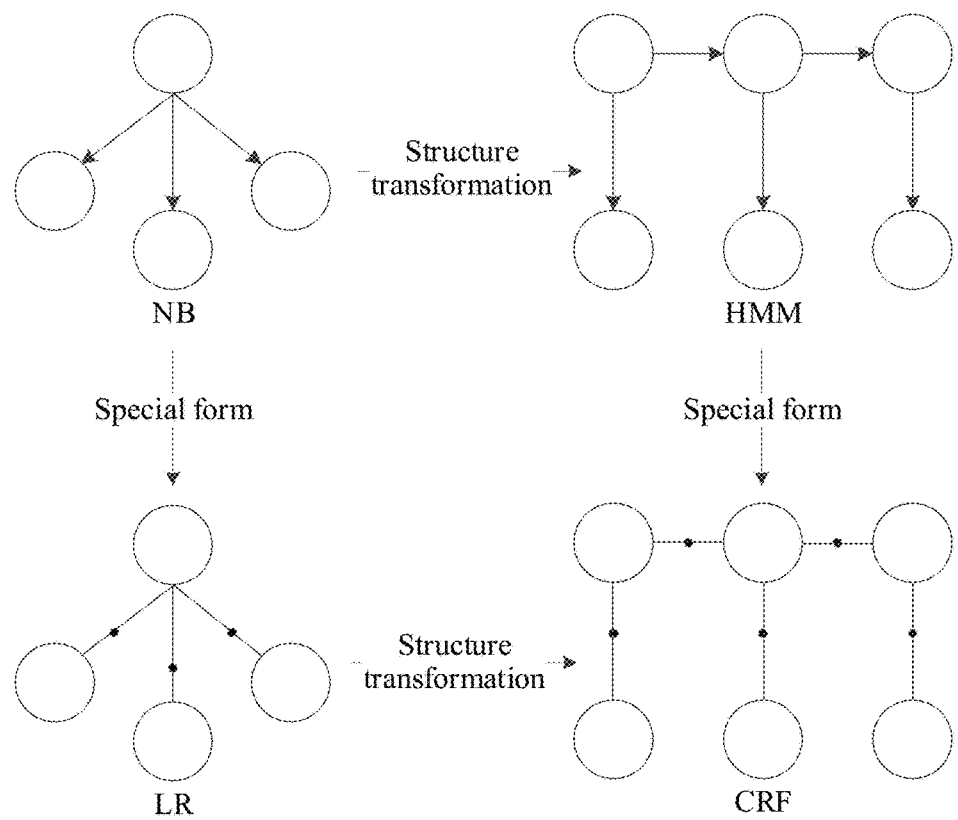
FIG. 1f is a schematic diagram of relationships between NB, HMM, CRF, and LR according to some embodiments of this application.

FIG. 1f is a schematic diagram of relationships between NB, HMM, CRF, and LR. As shown in the figure, the LR is a special form of the NB, and the CRF is a special form of the HMM, while different structures between the NB and the HMM lead to different structures between the LR and the CRF.

S105: Select, from the 3D images, target voxels of which the voxel type is a preset voxel type to obtain position information of the target voxels.

After step S104, types of all of the voxels in the 3D image may be determined, and a voxel of which the voxel type is the preset voxel type is selected as the target voxel from the 3D images. The preset voxel type may be a voxel type of interest, for example, a preset pathology type in the medical field, and the preset pathology type may be a breast tumor type, for example. Therefore, in this embodiment, the preset voxel type may be a breast tumor type, and correspondingly, a target region to be identified may be a breast tumor region.

Table 2 is an example of position information of the target voxel. The position information of the target voxel may include information such as coordinate positions and target voxel numbers corresponding to all of the target voxels of preset voxel types in the 3D image.

TABLE 2

| Target voxel number | 0x01 | 0x02 | 0x03 | 0x04 | 0x05 |
|---|---|---|---|---|---|
| Coordinate position | (a, b, c) | (d, e, f) | (g, h, i) | (j, k, 1) | (m, n, o) |

The position information corresponding to the target voxels in the 3D image may include the corresponding position information on any one or more of the 3D images, and the position information may be a coordinate position relative to the world coordinate system, a coordinate position relative to an internal coordinate system of the 3D images, and the like.

S106: Localize a target region based on the position information of the target voxels.

After the position information of the target voxels is acquired in step S105, the target region may be obtained through the position information of the target voxels, and then the target region is be displayed from a multi-directional angle, so as to facilitate actual observation and use of a user.

For example, in some embodiments, an imaging device may draw a table according to the position information of the target voxels, and display the position information of the target voxels in the form of a table.

For example, in some embodiments, an imaging device may calculate a volume of a lesion region according to a coordinate position of each target voxel in the position information of the target voxels.

The image region localization method provided by the embodiment of the present disclosure may be applied to a scenario in which tumors in a 3D magnetic resonance image are automatically identified. For example, according to the image region localization method provided by the embodiment of the present disclosure, image features of a plurality of 3D magnetic resonance images are extracted from a certain part of a patient's body, fused features are calculated according to these image features, and the tumor in the 3D magnetic resonance image may be analyzed in a plurality of directions based on the fused features, thereby achieving automatic identification of the tumor in the 3D magnetic resonance image.

A possible implementation of S106 may be to select a target 3D image from a plurality of 3D images, and then, based on the position information of the target voxels, the target region is localized on the target 3D image.

Based on the above, according to the embodiments of this application, a plurality of 3D images of a target part may be acquired, where the plurality of 3D images includes a plurality of 3D images of different modalities. Image features of the plurality of 3D images are extracted; The image features of the plurality of 3D images are fused to obtain fused features. Voxel types corresponding to voxels in the 3D images are determined according to the fused features. Target voxels of which the voxel type is a preset voxel type are selected from the 3D images to obtain position information of the target voxels. A target region is localized based on the position information of the target voxels. According to the solution, different image features (such as blood features, water molecule features, fat features, and the like) may be extracted from 3D images of different modalities, fused features including multi-modality information may be obtained according to the image features, and the target region can be directly localized according to the fused features. Therefore, the solution can reduce the probability of a false determination, thereby improving a localizing accuracy for image regions.

According to the method described in the foregoing embodiment, the following further provides detailed descriptions by using an example.

In the embodiment of this application, the image region localization apparatus is specifically integrated in the electronic device for description by way of example.

Figure 2A:
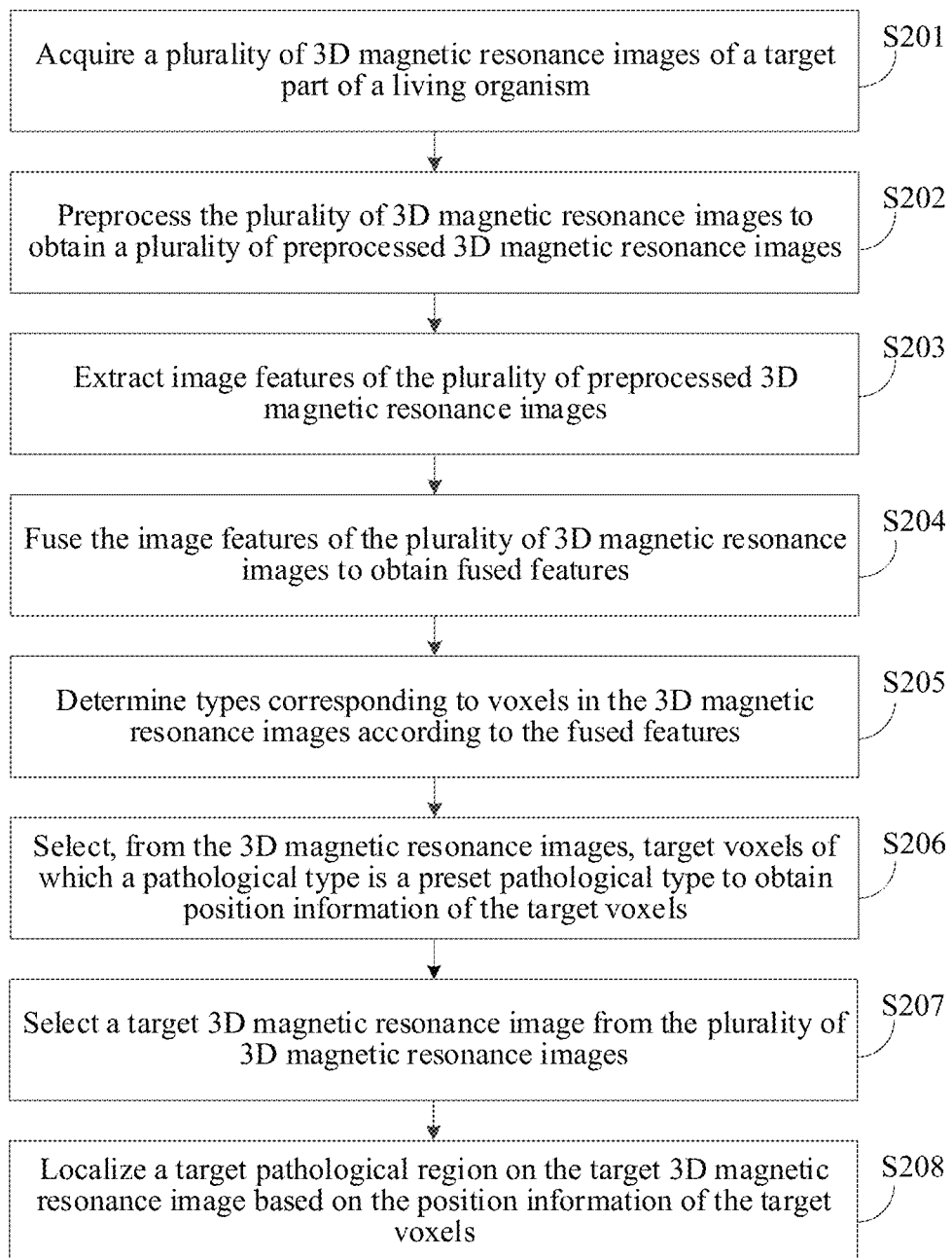
FIG. 2a is another schematic flowchart of the image region localization method according to some embodiments of this application.

The method of extracting image features of a plurality of 3D images in S102 may be preprocessing the plurality of 3D images to obtain a plurality of preprocessed 3D images; and extracting image features of the plurality of preprocessed 3D images. In this case, FIG. 2a is another schematic flowchart of an image region localization method according to some embodiments of this application. As shown in FIG. 2a, the electronic device may localize a pathological tissue region in a map according to the 3D magnetic resonance image. The electronic device localizes the region through the following process.

S201: Acquire a plurality of 3D magnetic resonance images of a target part of a living organism.

For a specific method for acquiring the plurality of 3D magnetic resonance images of the target part, refer to detailed operations in S101, and details are not described herein again.

S202: Preprocess the plurality of 3D magnetic resonance images to obtain a plurality of preprocessed 3D magnetic resonance images.

Since the plurality of acquired 3D images, such as the 3D magnetic resonance image of this embodiment, have different specifications such as dimensions and resolutions, in order to further improve the accuracy of pathological tissue identification, after the plurality of 3D images are acquired and before the image features of the plurality of 3D images are extracted, the plurality of 3D images may be preprocessed.

In some embodiments, the plurality of 3D images may not be in the same coordinate system. In order to further improve the accuracy of identification of the target region such as a pathological tissue, a registration operation of the coordinate system may be performed on the plurality of 3D images. The registration operation may be implemented through the following operations.

(1) Acquire a Reference Coordinate System and Original Coordinate Systems of a Plurality of 3D Images.

In order to describe the position of a voxel, a coordinate system of the voxel needs to be selected. In the reference coordinate system, in order to determine the position of the voxel in space, an ordered set of data, that is, coordinates, is selected according to a specified method. The reference coordinate system may include types such as a Cartesian rectangular coordinate system, a planar polar coordinate system, a cylindrical coordinate system, a spherical coordinate system, and the like. The reference coordinate system may specifically be a world coordinate system, a camera coordinate system, an image coordinate system, a voxel coordinate system, and the like.

The reference coordinate system is the method of specifying coordinates by preset rules, that is, the reference coordinate system used in the problem. The reference coordinate system may be pre-stored in a local internal memory, or may be inputted by the user.

The original coordinate system of the 3D image is acquired in various ways. For example, in some embodiments, a medical image processing device may mark the 3D image during acquisition, in another embodiment, the original coordinate system transmitted by an image acquisition device may be received, and in another embodiment, the original coordinate system may be inputted by the user.

For example, in some embodiments, the original coordinate system may also be acquired from a local storage or an external storage. For example, the original coordinate system of the 3D image may be acquired from a local image database such as a medical image data storage system. Alternatively, the original coordinate system of the 3D image is acquired through communication with other storage devices through a network.

(2) Transform the Original Coordinate Systems of the Plurality of 3D Images into the Reference Coordinate System.

The original coordinates of the voxel measured in the original coordinate system are transformed in the coordinate system to obtain representation of the original coordinates on the reference coordinate system. Currently, commonly used registration algorithms may be divided into overall registration and partial registration according to the process, such as an iterative closest point (ICP) algorithm.

A pair of voxels may be registered through pair-wise registration. In some embodiments, a preset 3D rotation matrix R is applied, so that the coordinates of the voxel and the reference coordinate system can be accurately registered.

$$\begin{pmatrix} x' \\ y' \\ z' \end{pmatrix} = R * \begin{pmatrix} x \\ y \\ z \end{pmatrix}$$

(x, y, z) are original coordinates of the 3D image, (x', y', z') are registered coordinates, and R is a third-order rotation matrix.

In some embodiments, in a case that a right-hand screw rule is used, rotation matrices of the rotation matrix R on an axis x, an axis y, and an axis z are respectively:

$$R_x = \begin{pmatrix} 1 & 0 & 0 \\ 0 & \cos\theta & -\sin\theta \\ 0 & \sin\theta & \cos\theta \end{pmatrix}$$

$$R_y = \begin{pmatrix} \cos\theta & 0 & \sin\theta \\ 0 & 1 & 0 \\ -\sin\theta & 0 & \cos\theta \end{pmatrix}$$

$$R_z = \begin{pmatrix} \cos\theta & -\sin\theta & 0 \\ \sin\theta & \cos\theta & 0 \\ 0 & 0 & 1 \end{pmatrix}$$

Rotation around any axis may be decomposed into a superposition of rotation around three coordinate axes, and the finally obtained rotation matrix R is a product of the above three matrices.

The preset 3D rotation matrix R may be preset and stored in the local internal memory by a person skilled in the art.

In some other embodiments, voxel spacings of the plurality of 3D images are different. In order to further improve the accuracy of identification of the pathological tissue, a registration operation may be performed on the plurality of 3D images in the following manner. The registration operation may be implemented through the following operations.

(2) Acquire a Reference Voxel Spacing and an Original Voxel Spacing of the Plurality of 3D Images.

The voxel spacing may describe density between voxels, which is also referred to as dot spacing, and specifically refers to a distance from a center of a certain voxel to a center of an adjacent voxel. Since the voxel spacing reflects a size of space between two voxels, smaller voxel spacing means smaller space between voxels, that is, higher voxel density and higher screen resolution.

Since resolution of the plurality of acquired 3D images may not be consistent, the accuracy of identification of a pathological tissue can be further improved by registering resolution of the plurality of 3D image.

The reference voxel spacing may be acquired in various ways. For example, in some embodiments, the reference voxel spacing may be set by inputting by a user. In another embodiment, the original voxel spacing of one 3D image may be selected from the plurality of 3D images as the reference voxel spacing. In another embodiment, the reference voxel spacing may also be acquired from a local storage or an external storage.

The original voxel spacing of the 3D image may also be acquired in various ways. For example, in some embodiments, an image acquisition device may mark the 3D image during acquisition. In another embodiment, the original voxel spacing transmitted by the image acquisition device may be received. In another embodiment, the original voxel spacing may be inputted by the user.

For example, in some embodiments, the original voxel spacing may also be acquired from a local storage or an external storage. For example, the original voxel spacing of the 3D image may be acquired from a local image database such as a medical image data storage system. Alternatively, the original voxel spacing of the 3D image is acquired through communication with other storage devices through a network.

(2) Transform the Original Voxel Spacing of the Plurality of 3D Images into the Reference Voxel Spacing.

The methods of voxel spacing registration are similar to voxel spacing registration, for example, an interpolation method, a gradient method, an optimization method, maximization of mutual information, and the like. In some embodiments, registration may be performed using the interpolation method such as nearest neighbor interpolation, double-line interpolation, three-line interpolation, and the like.

A principle of the interpolation-based method is to enlarge two images and have the same resolution by resampling, and to perform an interpolation operation during resampling, that is, to introduce new voxel data, so as to complete the registration.

In some embodiments, the nearest neighbor interpolation method is used for assigning a gray value of a nearest voxel to the original voxel, so as to perform the interpolation operation.

In some embodiments, the gray values of the four nearest points of voxels are used, and numerical values are calculated by linear equations, so that the interpolation operation is performed.

In some embodiments, corresponding weights are generated according to distances between a new sampling point and neighboring points, and the gray value of the new sampling point is interpolated by the gray value of each of the neighboring points according to the weights.

In some other embodiments, dimensions of the plurality of 3D images are different. In order to further improve the accuracy of identification of the pathological tissue, a registration operation may further be performed on the plurality of 3D images in the following manner. The registration operation may be implemented through the operations of:
  acquiring a reference dimension and original dimensions of the plurality of 3D images; and
  transforming the original dimensions of the plurality of 3D images into the reference dimension.

Since dimensions of the plurality of acquired 3D images may not be consistent, the accuracy of identification of a pathological tissue can be further improved by registering the dimensions of the plurality of 3D images.

The reference dimension is acquired in various ways. For example, in some embodiments, the reference dimension may be set by inputting by a user. In another embodiment, the original dimension of one 3D image may be selected from the plurality of 3D images as the reference dimension. In another embodiment, the reference dimension may also be acquired from a local storage or an external storage. The original dimension of the 3D image is acquired in various ways. For example, in some embodiments, an image acquisition device may mark the 3D image during acquisition. In another embodiment, the original dimension transmitted by the image acquisition device may be received. In another embodiment, the original dimension may also be inputted by the user.

The above three preprocessing operations, that is, the transformation operations of the coordinate system, the voxel spacing, and dimensions of the 3D images, may be implemented simultaneously without affecting the implementation sequence.

S203: Extract image features of the plurality of preprocessed 3D magnetic resonance images.

In this embodiment, a preset semantic segmentation network may be used for extracting the image features of the plurality of 3D images, so as to complete semantic segmentation of images, and one semantic category is allocated to each pixel in the inputted image to obtain a pixelated dense classification.

Commonly used semantic segmentation networks may include PSPNet, RefineNet, DeepLab, U-net, and the like. A general semantic segmentation architecture may be an encoder-decoder network architecture. The encoder may be a trained classification network, for example, a visual geometry group (VGG) and a residual neural network (ResNet). A difference between the architectures mainly lies in a decoder network. A task of the decoder is to semantically map discriminable features learned by the encoder to a pixel space to obtain dense classification.

Semantic segmentation requires not only discriminating ability at a pixel level, but also a mechanism that can map discriminating features learned by the encoder at different stages to the pixel space, for example, using skip connection and pyramid pooling as parts of a decoding mechanism.

In some embodiments, S202 may specifically include the following operations.

(1) Adopt a Preset 3D Convolutional Kernel to Perform Convolution Processing on the 3D Image:
  stacking continuous N-frame 2D images into a cube, and then adopting the 3D convolutional kernel to perform a convolution operation on the cube. In the structure, each feature map in the convolutional layer is connected to a plurality of adjacent consecutive frames in the previous layer, so that height information can be captured.

Specifically, a 3D convolutional kernel with a size of 1×1×1 is allowed to complete sliding of one row in an axis y from low to high on an axis x on a 5×5×5 3D image sequence with a step size of 1, then complete sliding of an image in an axis z from bottom to top on the axis y, and finally complete sliding of the entire 3D image sequence on the axis z from low to high. Each stop position is taken into a semantic segmentation network, and a category score of 5×5×5 positions can be obtained.

A preset 3D semantic segmentation model may be acquired from a locally stored model set or an externally stored model set. For example, the preset 3D semantic segmentation model may be acquired through communication with other storage devices through a network.

Since a 3D convolutional kernel provides only one weight, only one type of features can be extracted from the cube. Feature extraction obtained by one convolutional kernel is insufficient, so that a plurality of features may be identified by adding a plurality of convolutional kernels. A plurality of convolutional kernels are adopted, and each channel corresponds to a convolutional kernel, so that the 3D semantic segmentation model can extract a plurality of features of the 3D images.

(2) Adopt a Preset 3D Deconvolution Kernel to Up-Sample the Convolved 3D Image and Obtain Image Features of the 3D Image.

In a case that the 3D image is inputted into a preset 3D semantic segmentation model, the inputted 3D image may pass through a plurality of convolutional layers and down-sampling layers to obtain a heat map in the previous step, that is, a high-dimensional feature map, and then the high-dimensional feature map may pass a plurality of up-sampling layers in the current step to obtain the image feature.

There are a plurality of sampling methods, such as nearest neighbor interpolation, bilinear interpolation, mean interpolation, median interpolation, and the like. All of the methods can be used in the above operations of up-sampling and down-sampling.

S204: Fuse the image features of the plurality of 3D magnetic resonance images to obtain fused features.

For a specific implementation, refer to the detailed description in S103, and details are not described herein.

In some embodiments, S103 may specifically include the following operations.

(1) Acquire Preset Feature Weights Corresponding to the Image Features.

The preset feature weights may be stored in the preset 3D semantic segmentation model. The preset 3D semantic segmentation model may be acquired from a locally stored model set or an externally stored model set. For example, the preset 3D semantic segmentation model may be acquired through communication with other storage devices through a network.

(2) Accumulate and/or Multiply the Image Features of the Plurality of 3D Images Based on the Preset Feature Weights to Obtain Fused Features.

After the image features of the plurality of 3D images are acquired, the image features that reflect target region information in the target part from a plurality of angles may be fused by adopting the preset feature weights, and the obtained fused feature have accuracy and diversity.

Figure 2B:
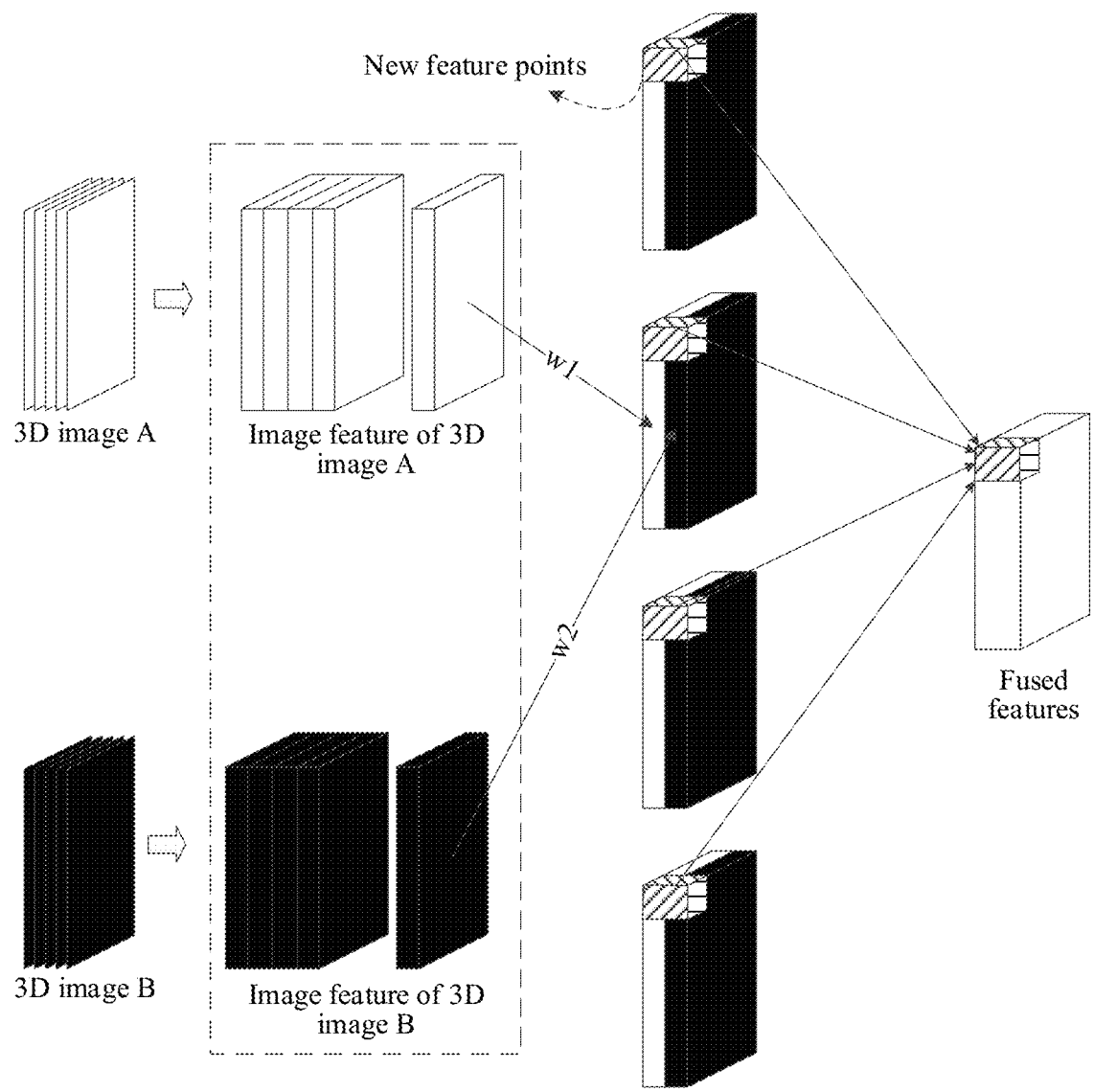
FIG. 2b is a schematic diagram of a feature fusion based on preset weights according to some embodiments of this application.

In some embodiments, FIG. 2b is a schematic diagram of feature fusion based on a preset weight. As shown in the figure, after features are extracted for a 3D image A and a 3D image B, feature points on the same layer and at the same position of the 3D image A and the 3D image B are serially fused based on preset weights w1 and w2 to obtain new feature points. After repetitions a plurality of times, the fused features of the 3D image A and the 3D image B can be obtained.

Figure 2C:
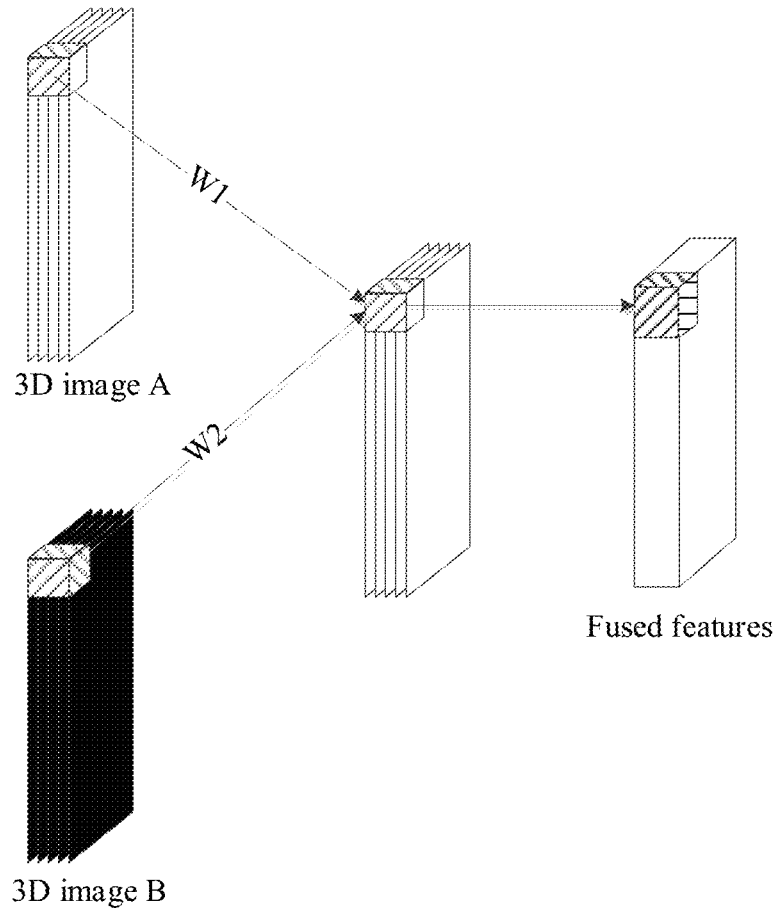
FIG. 2c is a schematic diagram of another feature fusion based on preset weights according to some embodiments of this application.

In some other embodiments, FIG. 2c is a schematic diagram of another feature fusion. As shown in the figure, in a case that image features of a plurality of 3D images are extracted in step S103, voxels on the same layer and at the same position of the 3D image A and the 3D image B are serially fused based on preset weights w1 and w2 to obtain fused features of the voxel according to the fusion result.

The preset feature weight may be preset and stored in the local internal memory by a person skilled in the art.

A possible implementation of weighting the image features of the plurality of 3D images based on the preset feature weights may be: determining a plurality of image features corresponding to the voxels at the same position in the plurality of 3D images; weighting the plurality of image features with the preset feature weights to obtain a plurality of weighted image features; and accumulating the plurality of weighted image features to obtain fused features of the voxels.

S205: Determine pathological types corresponding to voxels in the 3D magnetic resonance images according to the fused features.

It may be understood that in this embodiment, the 3D magnetic resonance image is processed to localize a pathological tissue region in the image. Therefore, the voxel type in this embodiment may be the pathological type. The pathological type may be a classification of diseases from the pathological point of view, which focuses on describing the current symptom. For example, the pathological type of the lung cancer may include small cell carcinoma, alveolar carcinoma, bronchial adenoma, and the like. For another example, the pathological type of a breast tumor may include a benign breast tumor and a malignant breast tumor. Further, the pathological type of the benign breast tumor may include fibroadenoma, intraductal papilloma, hamartoma, cyst, and the like. The pathological type of the malignant breast tumor may include lobular carcinoma in situ, intraductal carcinoma, mucinous adenocarcinoma, and the like.

A probability that the pathological type corresponding to the voxel in the 3D images are determined by using fused features. A dictionary may be adopted to query the pathological type corresponding to the probability, thus determining the pathological type corresponding to the voxel in the 3D image.

S206: Select, from the 3D magnetic resonance images, target voxels of which the pathological type is a preset pathological type to obtain position information of the target voxels.

For a specific implementation, refer to S105, and details are not described herein again.

S207: Select a target 3D magnetic resonance image from the plurality of 3D magnetic resonance images.

In order to better display the target voxels obtained in S205, the pathological tissues represented by the target voxels can be displayed on the 3D images, so that the target 3D images can be selected from the plurality of 3D images to display pathological tissues from a plurality of angles.

Since the plurality of 3D images may include image sequences of different modalities such as MRA, DWI, ADC, FS, DCE, and the like, the image sequences can produce MRI 3D images with different characteristics, which can not only reflect an anatomic form of a human body in a 3D space, but also reflect information about physiological functions such as human blood flow and cell metabolism.

One or more image sequences are selected from the image sequences of different modalities are used as target 3D images.

Selection can be performed in various ways. For example, in some embodiments, a target 3D image is selected according to a preset rule. For example, in some other embodiments, one or more image sequences are designated by a user from a plurality of image sequences of different modalities as target 3D images. For example, in some other embodiments, through communication with a network server through a network, a selection instruction sent by the network server is acquired, and one or more image sequences are selected as target 3D images according to the selection instruction.

In some embodiments, in order to display the pathological tissue represented by the target voxel more freely and flexibly, a preset 3D empty image may also be set as the target 3D image, and a dimension, resolution, and a value of each pixel of the preset 3D empty image may be preset by technicians or instantly set by the user. The preset 3D empty image may be saved in a local internal memory, or may be obtained from an external internal memory through the network, and may be generated locally after being set by the user.

S208: Localize a target pathological region on the target 3D magnetic resonance image based on the position information of the target voxels.

Based on the position information of the target voxels, the target region may be localized in various methods on the target 3D image. The first method may be as follows.

(1) Determine Corresponding Voxels on the Target 3D Image Based on the Position Information of the Target Voxels to Obtain the Corresponding Voxels.

Figure 2D:
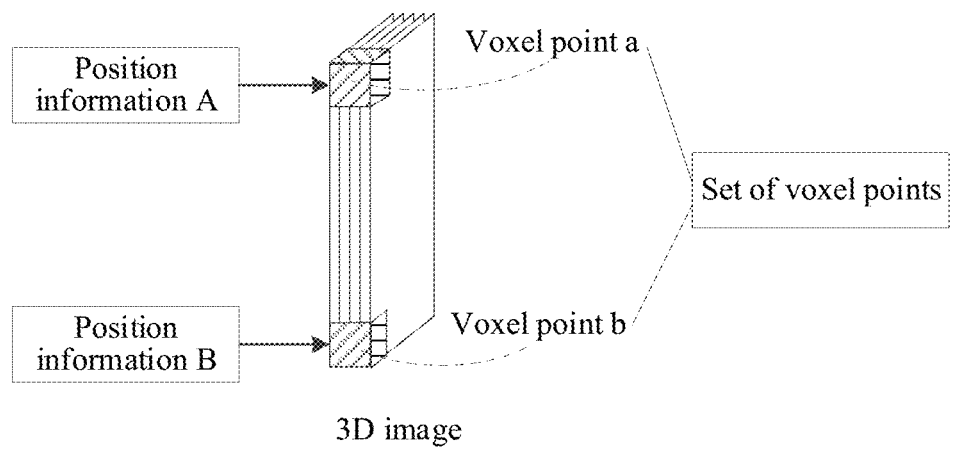
FIG. 2d is a schematic diagram of a scenario of determining corresponding voxels on a target image according to some embodiments of this application.

FIG. 2d is a schematic diagram of determining a corresponding voxel on a target MRI 3D image. As shown in the figure, a position corresponding to position information a is determined on the target MRI 3D image, and a voxel at the position is denoted as a voxel a. Similarly, a position corresponding to position information B is determined, and a voxel at the position is denoted as a voxel a.

The voxel a and the voxel b are the corresponding voxels on the target 3D image.

(2) Set a Voxel Value of Each of the Corresponding Voxels to a Preset Value to Identify the Target Region.

In S208, the target pathological region needs to be localized, that is, the target region is the target pathological region, and the target pathological region is identified by using the preset value. A type of the preset value may be a gray value, or may be an RGB (Red Green Blue) value, an RGBW (Red Green Blue White), or the like, which may be preset by a person skilled in the art or set instantly by a user.

A magnitude of the preset value may be saved in the local internal memory, or may be obtained from an external internal memory through the network, and may also be set by the user.

In some embodiments, in order to highlight an outline of the pathological tissue on the target 3D image and improve readability of the displayed image, the type of the preset value may be set to a gray value type with a magnitude of 1.

In some embodiments, in order to display an outline of the pathological tissue in bright red on the target 3D image and improve readability of the displayed image, for example, the type of the preset value may be set to an RGB type with a magnitude of #EE0000.

The second method may be as follows.
(1) Calculate a Mean of the Position Information of all of the Target Voxels to Obtain Position Information of a Central Point of the Target Region.

In S208, the target pathological region needs to be localized, that is, the target region is the target pathological region, and the position information of the central point of the target pathological region is obtained. A mean of the position information such as a coordinate and a relative position coordinate of the target voxels is calculated to obtain position information of centers of all of the target regions, that is, position information of a central point of a pathological tissue.

In some embodiments, in order to cause the central point to fall on the voxel in the 3D image, after the mean of the position information of the target voxels is calculated, a calculation result may be rounded off to obtain the position information of the central point of the pathological tissue.
(2) Localize the Central Point of the Target Region on the Target 3D Image Based on the Position Information of the Central Point.

The target region may be a target pathological region. The central point of the target pathological region on the target 3D image is localized in various ways. In some embodiments, coordinates of the central point may be directly displayed on a display interface. In another embodiment, the central point may be circled in the 3D image according to the position information of the central point.

It may be learned from above that, in the embodiment of this application, the following operations can be performed: acquiring a plurality of 3D magnetic resonance images of a target part of a living organism; preprocessing the plurality of transformed 3D magnetic resonance images to obtain a plurality of preprocessed 3D magnetic resonance images; extracting image features of the plurality of preprocessed 3D magnetic resonance images; fusing the image features of the plurality of 3D magnetic resonance images to obtain fused features; determining pathological types corresponding to voxels in the 3D magnetic resonance images according to the fused features; selecting, from the 3D magnetic resonance images, target voxels of which the pathological type is a preset pathological type to obtain position information of the target voxels; selecting a target 3D magnetic resonance image from the plurality of 3D magnetic resonance images; and localizing a target pathological region on the target 3D magnetic resonance image based on the position information of the target voxels. According to the solution, the 3D images of different modalities may be preprocessed, different image features (such as blood features, water molecule features, fat features, and the like) provided by the preprocessed images are extracted, fused features including multi-modality information may be obtained according to the image features, localizing is directly performed according to the fused feature, and a localized region of the pathological tissue is displayed on the target 3D image. Therefore, the solution can improve readability of the identification result and reduce the probability of a false determination for the pathological tissue, thereby improving an identification accuracy for pathological regions.

According to the method described in the previous embodiment, this embodiment is to provide a specific application scenario of region localizing. In this embodiment, the device for region localizing is specifically integrated in a picture archiving and communication system (PACS) to describe prediction of breast pathological tissues.

In the embodiment, the PACS is to automatically acquire a plurality of 3D magnetic resonance images of a chest part of a patient and extract image features of the 3D magnetic resonance images; then fuse the image features of the 3D magnetic resonance images to obtain fused features, and determine a pathological type corresponding to a voxel in the 3D magnetic resonance images according to the fused features; select, from the 3D magnetic resonance images, target voxels of which the pathological type is a breast tumor type to obtain position information of the target voxels; and performing pathological analysis of the chest part of the patient based on the position information of the target voxels to obtain pathological information of a breast tumor.
(I) Acquire a Plurality of 3D Magnetic Resonance Images of a Target Part.

The PACS is a system applied in an imaging department of a hospital. A main task of the system is to store various daily medical images, for example, images produced by magnetic resonance, CT, ultrasound, infrared instrument, microscope, and the like through various interfaces such as analog, DICOM, a network, and the like in a digital way. When necessary, the images can be quickly called under certain authorization, and some auxiliary diagnostic management functions can also be added.

In this embodiment, the PACS calls a DCE 3D sequence and a DWI 3D sequence of a target patient from the local internal memory.

Figure 3A:
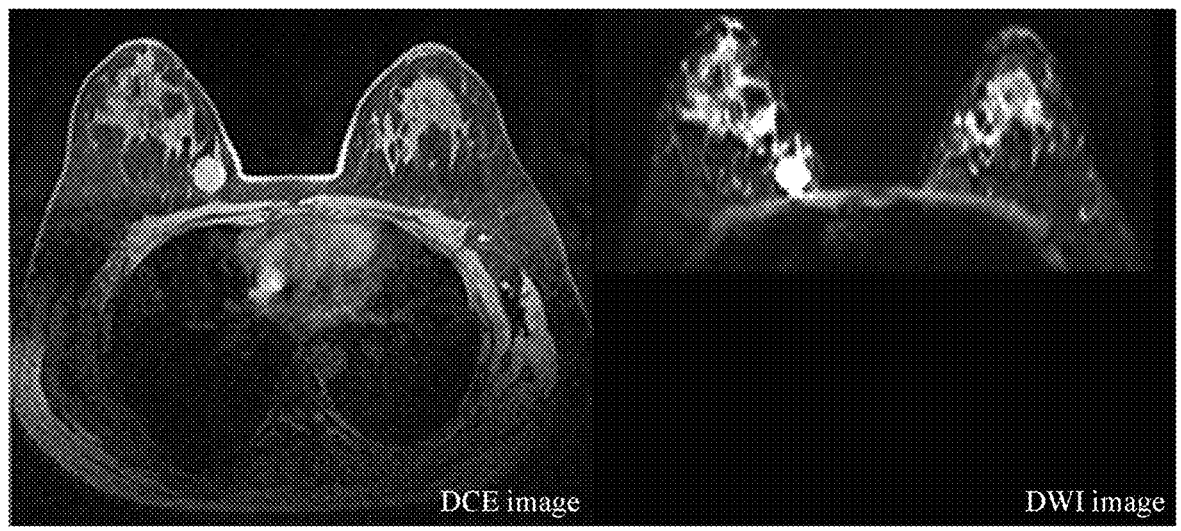
FIG. 3a is a schematic diagram of a DCE image and a DWI image according to some embodiments of this application.

FIG. 3a is a DCE image and a DWI image in a multi-modality MRI 3D image. As shown in the figure, a breast and an internal pathological breast tissue as well as a ribcage and internal organs such as an internal heart may be clearly seen in the DCE image. From the DWI sequence, only the pathological tissue of the breast and the interior can be clearly seen. Due to different compositions of the pathological tissue and the heart, the ribcage and the inner heart in the image are low signals, that is, a black part. Therefore, in this embodiment, the DCE 3D sequence and the DWI 3D sequence are used as multi-modality 3D magnetic resonance images to predict pathological tissues, and images of a breast and an internal breast pathological tissues can be directly obtained, while the ribcage and the internal heart are displayed in black. As a result, determination of the breast pathological tissues in the solution is not affected by the ribcage and the internal heart, and there is no need to cut out local parts of the images after acquiring multi-modality 3D magnetic resonance images to obtain breast images to reduce the influence on the heart.

In this embodiment, the PACS may also register the acquired DCE and DWI images to improve the identification accuracy for the pathological tissues.

The PACS denotes the DCE 3D sequence before contrast agent injection as DCE_T0, the DCE-MRI 3D sequence after contrast agent injection as DCE_Ti and the DWI 3D sequence as DWI_bi.

The letter i in the DCE_Ti represents a DCE sequence at an $i^{th}$ time point after the patient is injected with the contrast agent.

The letter b in the DWI_bi represents a diffusion sensitivity factor, and i represents a DWI sequence of an $i^{th}$ value b. A larger diffusion sensitivity factor indicates a larger contrast between the pathological tissue and a normal tissue.

Figure 3B:
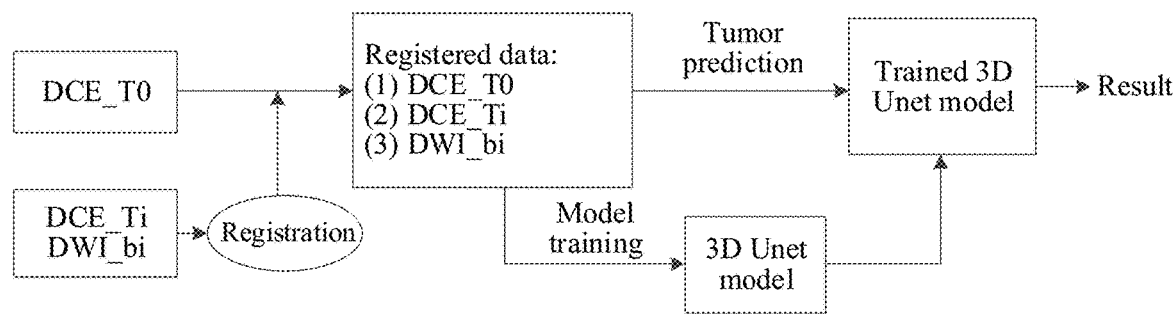
FIG. 3b is a schematic flowchart of a specific embodiment according to some embodiments of this application.

FIG. 3b is a flow chart of a specific embodiment according to this embodiment, which includes a tumor prediction part and a model training part. As shown in FIG. 3b, in the model training part, the PACS registers the acquired DWI_bi and DCE_Ti according to the acquired DCE_T0 to obtain a registered training image, and trains a 3D Unet model by using the images to obtain a trained 3D Unet model. In the tumor prediction part, the PACS registers the acquired DWI_bi and DCE_Ti according to the acquired DCE_T0, so that the resolution, image dimensions, and coordinate systems of DWI_bi, DCE_Ti, and DCE_T0 are the same, and then the registered data is inputted into the trained 3D Unet model to localize the pathological region. The following are detailed operations.

In this embodiment, the letter i in DCE_Ti is 3, and b is 600 and i is 800 in DWI_bi.

The PACS uses the current world coordinate system as the reference coordinate system, and registers the coordinate systems of DCE_T0, DCE_T3, and DWI_b800 to the current world coordinate system.

Then, the PACS registers other DCE 3D sequences and DWI 3D sequences by using a voxel spacing of DCE 3D sequences before contrast agent injection into a target patient as a reference voxel spacing. That is, the voxel spacing of DCE_T0 is used for registering the voxel spacing of DCE_T3 and DWI_b800 sequences.

The following are specific operations.

(1) DCE_T0 Registration:

An origin of the coordinate system of DCE_T0 acquired by the PACS is $(x_0, y_0, z_0)=(-182.3, 233.1, -35.28)$. The coordinates of DCE_T0 are transformed into the world coordinate system (x', y', z') by using a rotation matrix and the origin of the coordinate system:

$$(x',y',z')=DCE\_T0*R+(x_0,y_0,z_0)$$

The origin of the coordinate system $(x_0, y_0, z_0)$ is stored in an internal storage of the PACS and can be read from a DWI_b800 image in a case that the PACS acquires the image. A spatial rectangular coordinate system, that is, a right-hand coordinate system, is used as the current world coordinate system, and therefore a rotation matrix R is used as a rotation matrix:

[1, 0, 0]
[0, 1, 0]
[0, 0, 1]

A dimension of DCE_T0 acquired by the PACS is (x, y, z)=(448, 448, 72) voxels. Voxel spacings of DCE_T0 in directions x, y, and z are (0.84, 0.84, 1.6), which are denoted as reference voxel spacings.

(2) DCE_T3 Registration:

In an actual image acquisition process, since coordinate system parameters, dimension parameters, and voxel spacings of the DCE_Ti image are consistent, that is, parameters of DCE_T0 and DCE_T3 are consistent, so that it can be considered that data of DCE_T3 and DCE_T0 has been registered, and (x', y', z') is also the coordinate of DCE_T3 in the world coordinate system.

(3) DWI_b800 Registration:

An origin of the coordinate system of DWI_b800 is $(x_0, y_0, z_0)=(-176.1, 69.86, -49.61)$. Coordinates of DWI_b800 are transformed into the world coordinate system (x', y', z'):

$$(x',y',z')=DCE\_T0*R+(x_0,y_0,z_0)$$

R is a rotation matrix, and the origin of the coordinate system $(x_0, y_0, z_0)$ is stored in an internal storage of the PACS and can be read from a DWI_b800 image in a case that the PACS acquires the image.

The dimension of DWI_b800 is (x, y, z)=(192, 96, 32) voxels, where the voxel spacings in directions x, y and z are respectively (1.875, 1.875, 4.8). Since the reference voxel spacing is (0.84, 0.84, 1.6), and the registered voxel spacing dimension needs to be rounded to an integer, a voxel length of DWI_b800 in the direction x is 192×1.875÷0.84=429.

Similarly, a voxel length of DWI_b800 in the direction y is 96×1.875÷0.84-214, and a voxel length in the direction z is 32×4.8÷1.6=96.

Therefore, after DWI_b800 is transformed into (429, 214, 96) by using a 3D data linear interpolation method, the dimension needs to be further cut, that is, DWI_b800 with the dimension (429, 214, 96) is filled into a 3D empty matrix of (448, 448, 72), missing parts are filled with 0, and extra parts are removed.

The above DCE_T0, DCE_T3, and DWI_b800 are all 3D images. After the above three operations, three groups of 3D magnetic resonance images with the same dimension and the same coordinate system after registration can be obtained.

(II) Extract Image Features of the Plurality of 3D Magnetic Resonance Images.

In a case that a 2D U-Net model is used for processing the 3D images, due to poor performance of the model in consistency of processing the 3D images, 3D information cannot be used properly. Compared with a 3D U-Net (Three Dimensions U-Net) model, the 2D U-Net model has some problems such as tedious preprocessing, low efficiency, and inaccurate output results. Therefore, in this embodiment, the 3D U-Net model is used for processing the 3D images.

Figure 3C:
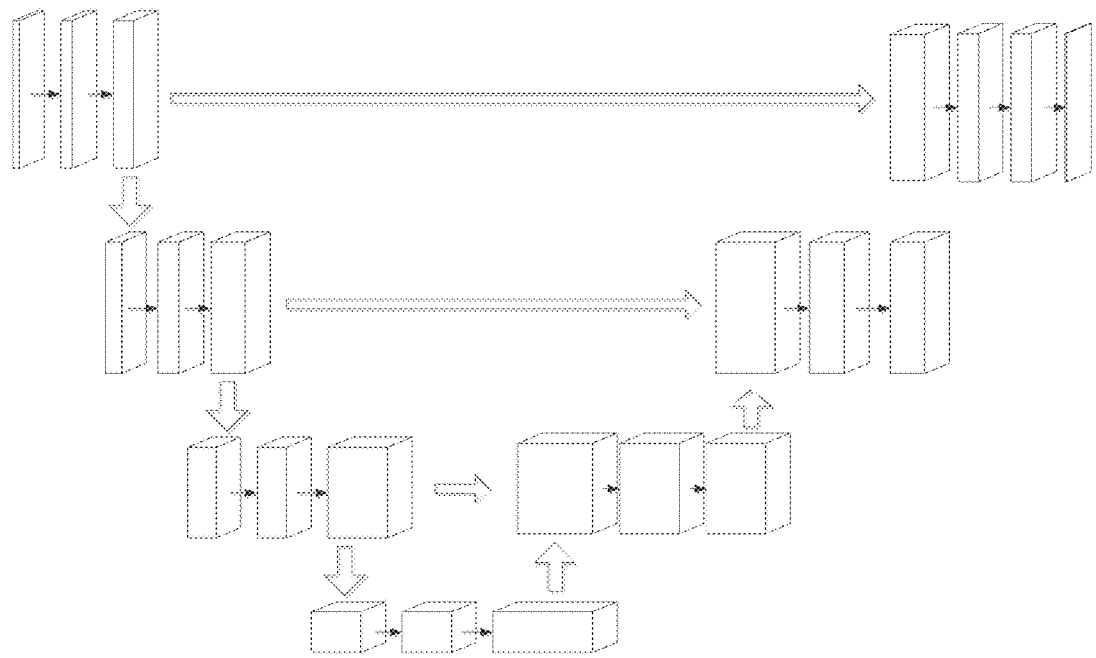
FIG. 3c is a schematic structural diagram of a 3D U-Net model according to some embodiments of this application.

FIG. 3c is a schematic structural diagram of a 3D U-Net model. As shown in the figure, the 3D U-Net model is based on a U-Net model, and all of the 2D operations in the network model are to be replaced by 3D operations, for example, 3D convolution, 3D pooling, 3D up-sampling, and the like. Similar to the U-Net model, the 3D U-Net model is also an encoding-decoding structure. An encoding terminal is configured to analyze global information of 3D images and extract and analyze features. Specifically, in this embodiment, the 3D U-Net model has been trained in advance, which includes and uses the following convolutional operations.

a. Each layer of a neural network includes two convolutional layers with dimensions of 3*3*3.
b. Batch Normalization (BN) causes the network to converge better.
c. A rectified linear unit (ReLU) follows each of the convolution layers.
d. A maximum of the dimension 2*2*2 is used for downsampling with a stride of 2.

Correspondingly, a decoding terminal is configured to repair target details, and the following operations are included and performed before the last layer of the decoding terminal.

a. Each layer of the neural network includes a 2*2*2 deconvolution layer for up-sampling with a stride of 2.

b. Two 3*3*3 convolutional layers follow each deconvolution layer.

c. A rectified linear unit follows each of the convolution layers.

e. In addition, it is necessary to use the result of the network layer corresponding to the coding terminal as a part of inputs of the decoding terminal, so as to acquire high-voxel feature information, so that images can be synthesized better.

For the 3D images, it is not necessary to input each 2D slice separately, but the whole 3D image can be inputted into the 3D U-Net model. Therefore, the 3D images of DCE_T0, DCE_T3, and DWI_b800 obtained in the previous step are used as three channels of inputted data, and the corresponding image features can be extracted by inputting the trained 3D U-net model.

(III) Fuse the Image Features of the Plurality of 3D Magnetic Resonance Images to Obtain Fused Features.

At the last layer of the decoding terminal of the 3D U-Net model, a 1*1 convolutional kernel is used for convolutional operation, and each 64-dimensional feature vector is mapped to an output layer of the network. In the previous step, the image features of the DCE_T0 3D image, the DCE_T3 3D image, and the DWI_b800 3D image are extracted, and the image features are mapped to the output layer of the network at the last layer of the decoding terminal of 3D U-Net model, so that the fused features are obtained.

(IV) Determine Pathological Types Corresponding to Voxels in the 3D Magnetic Resonance Images According to the Fused Features.

After the fused feature is acquired, at the output layer of the 3D U-Net model, a probability that the pathological type corresponds to the voxel in the 3D magnetic resonance image may be determined according to the fused features.

In this embodiment, in order to reduce the influence of the value range of the fused features on the final result, balance the value range of the features, and improve the accuracy of identifying pathological tissues, it is necessary to normalize the range of the features in advance by using a max-min normalization method to normalize the values of the features to an interval of [0, 1]:

$$x' = (x - x_{min})/(x_{max} - x_{min})$$

$x_{max}$ is a maximum value of sample data, $x_{min}$ is a minimum value of sample data, and x' is a normalized result.

According to the above operations, after the probability that the pathological type corresponding to the voxel in the 3D magnetic resonance images is determined by using the fused features, a preset pathological dictionary is adopted to query the pathological type corresponding to the probability, thus determining the pathological type corresponding to the voxel in the 3D magnetic resonance image.

The preset pathological dictionary is stored in the local internal memory of PACS, and the pathological type corresponding to the voxel in the 3D magnetic resonance images can be determined by calling the preset pathological dictionary.

Table 3 is a format example of the preset pathological dictionary. As shown in the table, the obtained probabilities are respectively 0, (0, x], (x, y), [y, 1), and 1. The pathological type corresponding to the probability 0 is A, the pathological type corresponding to the probability greater than 0 and less than or equal to x is B, the pathological type corresponding to the probability greater than x and less than y is C, the pathological type corresponding to the probability greater than or equal to y and less than 1 is D, and the pathological type corresponding to the probability of 1 is E.

TABLE 3

| Probability | 0 | (0, x] | (x, y) | [y, 1) |
|---|---|---|---|---|
| Pathological type | Viscera | Neither viscera nor tumor | Benign breast tumor | Maglignant breast tumor |

(V) Select, from the 3D Magnetic Resonance Images, Target Voxels of which the Pathological Type is a Preset Pathological Type to Obtain Position Information of the Target Voxels.

After step (4), the pathological types of all of the voxels in the 3D magnetic resonance image can be determined, and voxels of which the pathological type is the malignant breast tumor type are selected from the 3D magnetic resonance images as target voxels. Table 4 is an example of position information of target voxels. The position information of the target voxels may include coordinate values of target voxels of all of the malignant breast tumor types in the 3D images.

TABLE 4

| Target voxel number | 0x01 | 0x02 | 0x03 | ... 0x0N |
|---|---|---|---|---|
| Coordinate value | (a, b, c) | (d, e, f) | (g, h, i) | ... (m, n, o) |

(VI) Localize a Target Pathological Region Based on the Position Information of the Target Voxels.

If the pathological type is the malignant breast tumor type, the target pathological region is a malignant breast tumor region. If the pathological type is the breast tumor type, the target pathological region is a breast tumor region, and the like.

In this embodiment, a DCE_T0 image and a preset 3D empty image are selected from the plurality of 3D magnetic resonance images as target 3D magnetic resonance images.

The dimension and resolution of the preset 3D empty image are the same as those of the DCE_T0 image, and a type of each pixel is a gray value of 0. The preset 3D empty image is saved in the local internal memory of the PACS.

According to the position information of the target voxels obtained in step (5), the coordinate values of all of the target voxels are applied to the DCE_T0 image, a set of corresponding voxels are obtained from the DCE_T0 image, and the values of the voxels are set to a gray value of 1, so as to highlight the outline of pathological tissues on the DCE T0 image and improve readability of the displayed image.

Similarly, the coordinate values of all of the target voxels are applied to the preset 3D empty image, a set of corresponding voxels are obtained from the preset 3D empty image, and the values of the voxels are set to a gray value of 1, so as to highlight the outline of pathological tissues on the preset 3D empty image and improve readability of the displayed image.

Then, a mean of coordinate values of all of the target voxels is calculated and rounded off to obtain coordinates (X,Y) of a central point of pathological tissues. According to the coordinates of the central point, voxel values at coordinates (X, N) and (N, Y) are set to 0.8, so as to display locations of the central point on the DCE_T0 image and the preset 3D empty image and display the value of the central point on the preset 3D empty image.

Figure 3D:
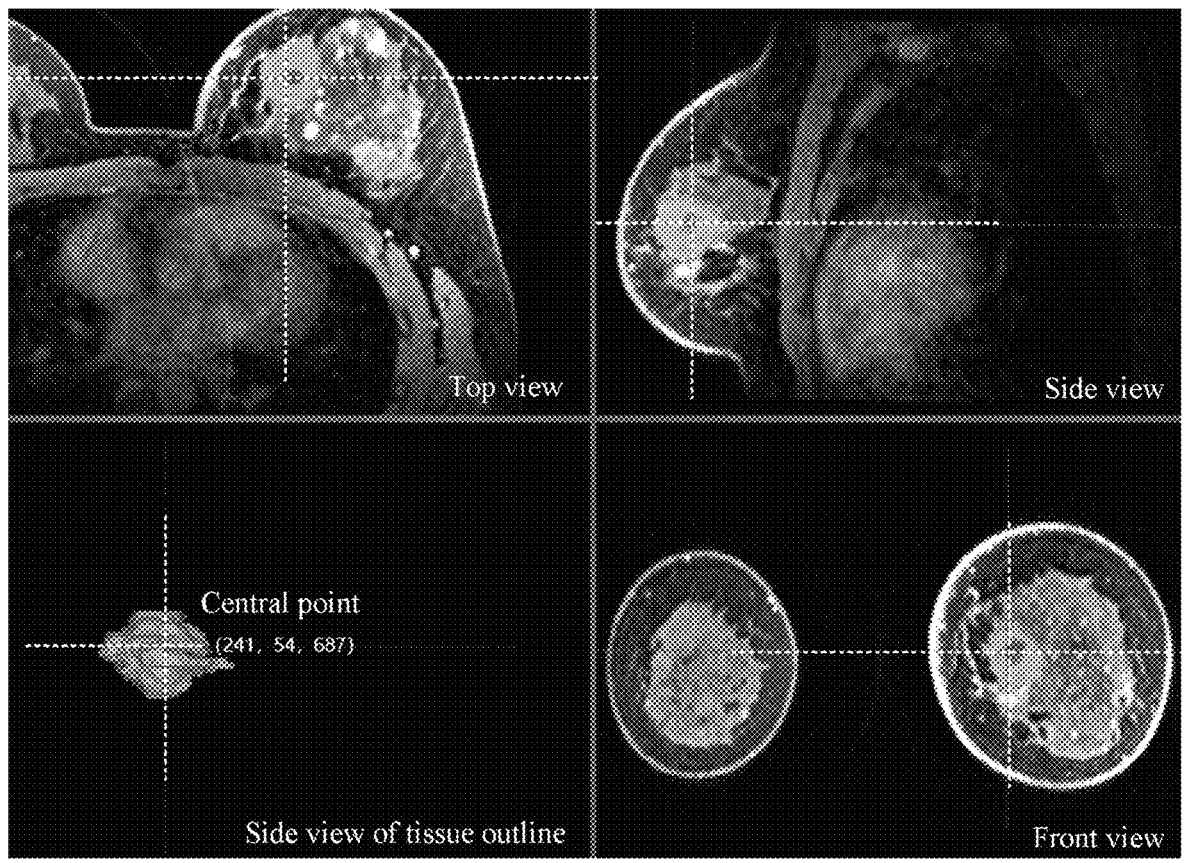
FIG. 3d is a schematic diagram of outputs according to some embodiments of this application.

FIG. 3d is an output result provided by this embodiment, which shows three views of a pathological tissue outline displayed on the DCE_T0 image and a side view of the pathological tissue outline on the preset 3D empty image. All of the pathological tissue outlines are highlighted, central points are displayed with a cross on all of the images, and values of the central point are marked on the preset 3D empty image.

It may be learned from above that the PACS acquires a plurality of 3D magnetic resonance images of a chest part of a patient from a local internal memory, including the operations of: extracting image features of the plurality of 3D magnetic resonance images; then fusing the image features of the plurality of 3D magnetic resonance images to obtain fused features, and determining a pathological type corresponding to a voxel in the 3D magnetic resonance images according to the fused features; selecting, from the 3D magnetic resonance images, target voxels of which the pathological type is a breast tumor type to obtain position information of the target voxels; and localizing a breast tumor region based on the position information of the target voxels. In the embodiment of this application, since different pathological tissues have different physiological features (such as water content, fat ratio, blood content, and the like), the PACS can extract different image features (such as blood features, water molecule features, fat features, and the like) provided by 3D magnetic resonance images of different modalities, obtain fused features including multi-modality information according to the image features, and directly localizes the breast tumor region according to the fused features. Therefore, the solution can reduce the probability of a false determination of other tissues and organs as pathological tissues, thereby improving a localizing accuracy for pathological regions.

In order to better implement the above method, some embodiments of this application further provide an image region localization apparatus. The image region localization apparatus may be specifically integrated in an electronic device. The electronic device may include a magnetic resonance image acquisition device, a magnetic resonance imaging device, a medical image data processing device, a medical image data storage device, and the like.

Figure 4:
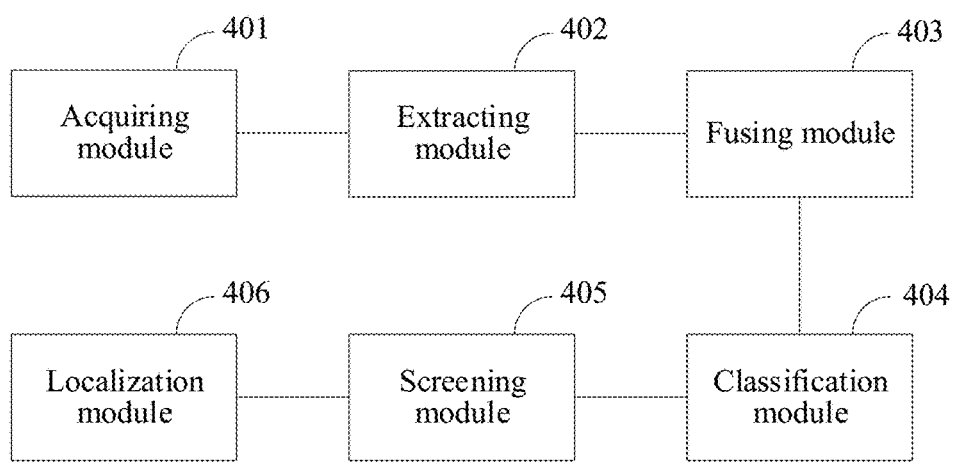
FIG. 4 is a schematic structural diagram of an image region localization apparatus according to some embodiments of this application.

For example, as shown in FIG. 4, the image region localization apparatus may include an acquiring module 401, an extracting module 402, a fusing module 403, a classification module 404, a screening module 405, and a localization module 406 as follows.

The acquiring module 401 is configured to acquire a plurality of 3D images of a target part, the plurality of 3D images including a plurality of 3D images of different modalities.

The extracting module 402 is configured to extract image features of the plurality of 3D images.

The fusing module 403 is configured to fuse the image features of the plurality of 3D images to obtain fused features.

The classification module 404 is configured to determine voxel types corresponding to voxels in the 3D images according to the fused features.

The screening module 405 is configured to select target voxels of which the voxel type is a preset voxel type from the 3D images to obtain position information of the target voxels.

The localization module 406 is configured to localize a target region based on the position information of the target voxels.

(1) In some embodiments, the extracting module 402 may include a preprocessing module and an extracting submodule as follows.

The preprocessing module is configured to preprocess the plurality of 3D images to obtain a plurality of preprocessed 3D images.

The extracting submodule is configured to extract image features of the plurality of preprocessed 3D images.

In some embodiments, the extracting submodule may be specifically configured to:
acquire a reference coordinate system and original coordinate systems of a plurality of 3D images; and
transform the original coordinate systems of the plurality of 3D images into the reference coordinate system.

In some other embodiments, the extracting submodule may be specifically configured to:
acquire a reference voxel spacing and an original voxel spacing of the plurality of 3D images; and
transform the original voxel spacing of the plurality of 3D images into the reference voxel spacing.

In some other embodiments, the extracting submodule may further be specifically configured to:
acquire a reference dimension and original dimensions of the plurality of 3D images; and
transform the original dimensions of the plurality of 3D images into the reference dimension.

(2) In some embodiments, the fusing module 403 may include a weight acquiring module and a weighted module as follows.

The weight acquiring module is configured to acquire preset feature weights corresponding to the image features.

The weighted module is configured to weight the image features of the plurality of 3D images based on the preset feature weights.

In some embodiments, the weighted module may be specifically configured to:
determine a plurality of image features corresponding to voxels at the same position in the plurality of 3D images;
weight the plurality of image features with the preset feature weights to obtain a plurality of weighted image features; and
accumulate the plurality of weighted image features to obtain fused features of the voxels.

(3) In some embodiments, the classification module 404 may include:
a determining module configured to determine the fused feature corresponding to each of the voxels in the 3D image;
a probability module configured to calculate a probability that the fused feature corresponding to the each voxel is of each voxel type to obtain a probability that the each voxel is of each voxel type; and
a classification submodule configured to determine the voxel type corresponding to the each voxel according to the probability of each voxel type.

(4) In some embodiments, the localization module 406 may include an image selection module and a localization submodule as follows.

The image selection module is configured to select a target 3D image from the plurality of 3D images.

The localization submodule is configured to localize a target region on the target 3D image based on the position information of the target voxels.

In some embodiments, the localization submodule may be specifically configured to:
determine corresponding voxels on the target 3D image based on the position information of the target voxels to obtain the corresponding voxel; and
set a voxel value of each of the corresponding voxels to a preset value to identify the target region.

In some other embodiments, the localization submodule may be specifically configured to:

calculate a mean of the position information of all of the target voxels to obtain position information of a central point of the target region; and localize the central point of the target region on the target 3D image based on the position information of the central point.

During specific implementation, the foregoing modules may be implemented as independent entities or may be randomly combined as a same entity or several entities for implementation. For specific implementations of the foregoing modules, refer to the foregoing method embodiments. Details are not provided herein again.

It may be learned from above that, in the image region localization apparatus in this embodiment, the acquiring module 401 is configured to acquire a plurality of 3D images of a target part. The extracting module 402 is configured to extract image features of the plurality of 3D images; The fusing module 403 is configured to fuse the image features of the plurality of 3D images to obtain fused features. The classification module 404 is configured to determine voxel types corresponding to voxels in the 3D images according to the fused features. The screening module 405 is configured to select target voxels of which the voxel type is a preset voxel type from the 3D images to obtain position information of the target voxels. The localization module 406 is configured to localize a target region based on the position information of the target voxels. According to the solution, different image features provided by the 3D images of different modalities may be extracted, fused features including multi-modality information may be obtained according to the image features, and the region can be directly localized according to the fused features. Therefore, the solution can reduce the probability of a false determination, thereby improving a localizing accuracy for regions.

Moreover, some embodiments of the present disclosure also provide a medical image processing device, including an image acquisition unit, a processor, and a memory. The memory stores a plurality of instructions. The medical image processing device can have integrated functions such as image acquisition, image analysis, and lesion localization.

The medical image acquisition unit may be configured to acquire a plurality of 3D images of a target part of a living organism.

The memory may be configured to store image data and a plurality of instructions.

The processor may be configured to read the plurality of instructions stored in the memory to perform the operations of:

loading the instructions from the memory for acquiring a plurality of 3D images of a target part, the plurality of 3D images including a plurality of 3D images of different modalities;

extracting image features of the plurality of 3D images;

fusing the image features of the plurality of 3D images to obtain fused features;

determining voxel types corresponding to voxels in the 3D images according to the fused features;

selecting, from the 3D images, target voxels of which the voxel type is a preset voxel type to obtain position information of the target voxels; and localizing a target region based on the position information of the target voxels.

In some embodiments, in executing the operation of determining voxel types corresponding to voxels in the 3D images according to the fused features, the processor specifically performs the operations of: determining a fused feature corresponding to each of the voxels in the 3D images; calculating a probability that the fused feature corresponding to the each voxel is of each voxel type to obtain a probability that the each voxel is of each voxel type; and determining the voxel type corresponding to the each voxel according to the probability that the each voxel is of each voxel type.

In some embodiments, in executing the operation of fusing the image features of the plurality of 3D images, the processor specifically performs the operations of: acquiring preset feature weights corresponding to the image features; and weighting the image features of the plurality of 3D images based on the preset feature weights.

In some embodiments, in executing the operation of weighting the image features of the plurality of 3D images based on the preset feature weights, the processor specifically performs the operations of: determining a plurality of image features corresponding to voxels at the same position in the plurality of 3D images; weighting the plurality of image features with the preset feature weights to obtain a plurality of weighted image features; and accumulating the plurality of weighted image features to obtain fused features of the voxels.

In some embodiments, in executing the operation of localizing a target region based on the position information of the target voxels, the processor specifically performs the operations of: selecting a target 3D image from the plurality of 3D images; and localizing the target region on the target 3D image based on the position information of the target voxels.

In some embodiments, in executing the operation of localizing the target region on the target 3D image based on the position information of the target voxels, the processor specifically performs the operations of: determining corresponding voxels on the target 3D image based on the position information of the target voxels to obtain the corresponding voxels; and setting a voxel value of each of the corresponding voxels to a preset value to identify the target region.

In some embodiments, in executing the operation of localizing the target region on the target 3D image based on the position information of the target voxels, the processor specifically performs the operations of: calculating a mean of the position information of all of the target voxels to obtain position information of a central point of the target region; and localizing the central point of the target region on the target 3D image based on the position information of the central point.

In some embodiments, in executing the operation of extracting image features of the plurality of 3D images, the processor specifically performs the operations of: preprocessing the plurality of 3D images to obtain a plurality of preprocessed 3D images; and extracting image features of the plurality of preprocessed 3D images.

In some embodiments, in executing the operation of preprocessing the plurality of 3D images, the processor specifically performs the operations of: acquiring a reference coordinate system and original coordinate systems of the plurality of 3D images; and transforming the original coordinate systems of the plurality of 3D images into the reference coordinate system.

The image region localization apparatus provided in the above embodiments can also be configured to localize a breast tumor region. In this case, the acquiring module 401 is configured to acquire a plurality of 3D images of a target part, the plurality of 3D images including a plurality of 3D images of different modalities.

The extracting module 402 is configured to extract image features of the plurality of 3D images.

The fusing module 403 is configured to fuse the image features of the plurality of 3D images to obtain fused features.

The classification module 404 is configured to determine voxel types corresponding to voxels in the 3D images according to the fused features.

The screening module 405 is configured to select, from the 3D images, target voxels of which the voxel type is a breast tumor type to obtain position information of the target voxels.

The localization module 406 is configured to localize a breast tumor region based on the position information of the target voxels.

Correspondingly, the processor of the above medical image processing device is configured to read the plurality of instructions stored in the memory to perform the operations of:

acquiring a plurality of 3D images of the target part, the plurality of 3D images comprising a plurality of 3D images of different modalities;

extracting image features of the plurality of 3D images; fusing the image features of the plurality of 3D images to obtain fused features;

determining voxel types corresponding to voxels in the 3D images according to the fused features; selecting, from the 3D images, target voxels of which the voxel type is a breast tumor type to obtain position information of the target voxels; and localizing a breast tumor region based on the position information of the target voxels.

Figure 5A:
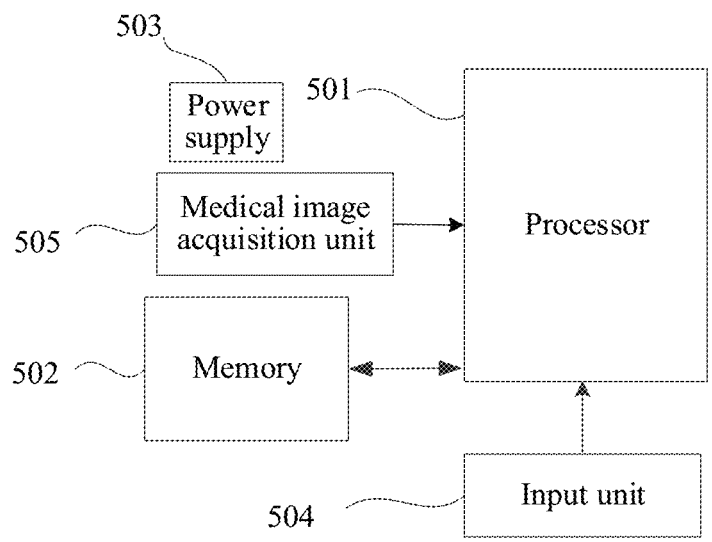
FIG. 5a is a schematic diagram of an internal structure of a medical image processing device according to some embodiments of this application.

FIG. 5a is a schematic diagram of an internal structure of a medical image processing device according to some embodiments of the present invention. Specifically:

Specifically, the medical image processing device may include components such as a processor 501 with one or more processing cores, a memory 502 with one or more computer-readable storage media, a power supply 503, an input unit 504, and an image acquisition unit 505. A person skilled in the art may understand that the structure of the medical image processing device shown in FIG. 5a does not constitute a limitation to the medical image processing device, and the medical image processing device may include more components or fewer components than those shown in the figure, or some components may be combined, or a different component deployment may be used. Here:

The processor 501 is the control center of the medical image processing device, and is connected to various parts of the medical image processing device by using various interfaces and lines. By running or executing the software program and/or module stored in the memory 502, and invoking data stored in the memory 502, various functions and data processing of the medical image processing device are performed, thereby performing overall monitoring on the medical image processing device. In some embodiments, the processor 501 may include one or more processing cores, and preferably, the processor 501 may integrate an application processor and a modem processor. The application processor mainly processes an operating system, a user interface, an application program, and the like, and the modem processor mainly processes wireless communication. It may be understood that the foregoing modem may either not be integrated into the processor 708.

The memory 502 may be configured to store a software program and a module, and the processor 501 runs the software program and the module that are stored in the memory 502, to implement various functional applications and data processing. The memory 502 may mainly include a program storage area and a data storage area. The program storage area may store an operating system, an application program required by at least one function (for example, a sound playback function and an image display function), and the like. The data storage area may store data created according to use of the medical image processing device, and the like. In addition, the memory 702 may include a high speed random access memory, and may also include a non-volatile memory, such as at least one magnetic disk storage device, a flash memory, or another volatile solid-state storage device. Correspondingly, the memory 502 may further include a memory controller, so that the processor 501 may access the memory 502.

The medical image processing device further includes the power supply 503 for supplying power to the components. Preferably, the power supply 503 may be logically connected to the processor 501 by using a power management system, thereby implementing functions such as charging, discharging, and power consumption management by using the power management system. The power supply 709 may further include one or more of a direct current or alternating current power supply, a re-charging system, a power failure detection circuit, a power supply converter or inverter, a power supply state indicator, and any other components.

The medical image processing device may further include an input unit 504. The input unit 504 may be configured to receive information about an inputted number or character, and generate inputs of a keyboard, a mouse, a joystick, an optical or trackball signal that are related to user settings and function control.

The image acquisition unit 505 includes a magnet, a gradient subunit, a radio frequency subunit, and the like. Main technical performance parameters of the above are a magnetic induction intensity, magnetic field uniformity, magnetic field stability, a spatial range of a fringe field, a magnetic induction intensity and linearity of a gradient field, sensitivity of a radio frequency coil, and the like, which are responsible for generation, detection, and encoding of magnetic resonance signals, that is, acquisition of 3D magnetic resonance images.

Figure 5B:
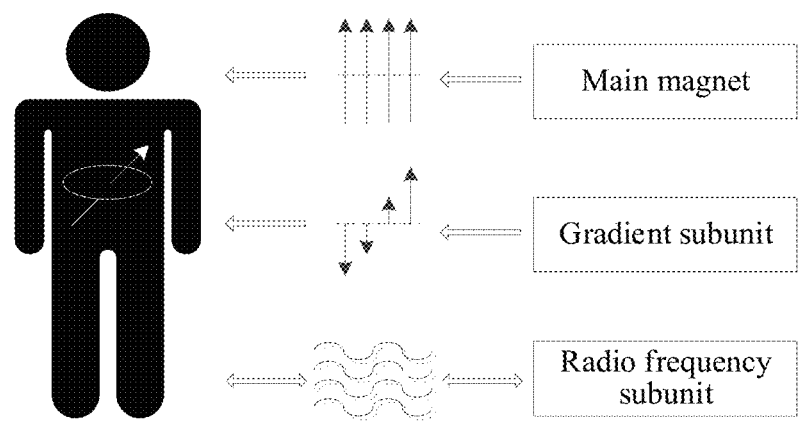
FIG. 5b is a schematic principle diagram of an acquisition unit according to some embodiments of this application.

The image acquisition unit 505 may superimpose a gradient magnetic field on a static magnetic field, and can arbitrarily change a gradient direction of the gradient magnetic field, thereby successfully performing thin-layer selective excitation and resonance frequency spatial encoding. FIG. 5b is a schematic diagram of a principle of an image acquisition unit 505. The image acquisition unit 505 may include physical components such as a main magnet, a radio frequency subunit, and a gradient subunit.

The main magnet is configured to generate field strength, that is, a main magnetic field. Types of the main magnet can be divided into a permanent magnet, a resistive magnet, a superconducting magnet, and the like. For example, in a case that a person's body or a part of the body is placed in the main magnetic field, nuclear spin polarization associated with the hydrogen nuclei in the body's tissue water occurs.

The gradient subunit can generate a gradient magnetic field to generate an NMR signal echo signal, perform spatial positioning encoding of an NMR signal and flow velocity phase encoding of a flowing liquid, and apply a diffusion-sensitive gradient field during DWI imaging, and the like. In some embodiments, the gradient subunit may include a gradient coil, a gradient amplifier, a digital-to-analog converter, a gradient controller, a gradient cooler, and the like.

The radio frequency subunit is responsible for transmitting, amplifying, and receiving to excite the hydrogen nuclei in a living organism or a non-living organism to generate and receive a magnetic resonance signal. The radio frequency subunit may include a radio frequency generator, a radio frequency amplifier, and a radio frequency coil. In some embodiments, in order to cause the transmitted radio frequency signal to be uniform, the radio frequency coil of the medical image processing device may be a quadrature coil. In some other embodiments, in order to achieve the signal-to-noise ratio, a surface coil may be used. In some other embodiments, a phased array surface coil and an integrated phased array surface coil may also be used.

The actual process of acquiring a 3D magnetic resonance image of a living organism or a non-living organism may be divided into two operations. The first operation is thin-layer selective excitation and spatial encoding, and then useful information contained in an encoding capacity is determined.

In some embodiments, simplest imaging is adopted, that is, single thin layer imaging, including the operations of: causing core in a thin layer to be studied to be selectively excited, and encoding information obtained from the thin layer in two dimensions; and determining a thickness of the thin layer through a gradient slope and a width of a RF pulse.

In some embodiments, spatial encoding in a single thin layer may be performed by using two-dimensional high-resolution spectroscopy. The spatial encoding method in a thin layer is to first apply a phase encoding gradient and then apply frequency encoding or a readout gradient to a series of polarized spins in the thin layer.

Specifically, the thin layer selection gradient is disconnected, and a second orthogonal gradient Gy is applied within a fixed period of time t. The nuclear processes at different frequencies are simultaneously determined by positions relative to the second gradient. A final result of phase encoding is distance information along a direction Y. After phase encoding, the gradient is disconnected, and then a third gradient Gx that is orthogonal to the first two gradients is applied and encoded only at a selected appropriate time t_x. Frequency values are properly and continuously changed to finally provide a spatial code along an axis X. As long as the value of the phase encoding gradient is gradually increased, the process can be repeated.

Although not shown, the medical image processing device may further include a display unit, a cooling system, and the like, and details are not described herein again.

The medical image processing device may specifically include one or more instruments.

In some embodiments, the medical image processing device may specifically be constituted by an instrument such as a nuclear magnetic resonance spectrometer, a nuclear magnetic resonance medical image processing device, and the like. For example, in a medical magnetic resonance imaging device, a processor 501, a memory 502, a power supply 503, an input unit 504, and an image acquisition unit 505 are embedded in the medical magnetic resonance imaging device.

In some other embodiments, the medical image processing device may further be specifically constituted by a plurality of instruments such as a nuclear magnetic resonance image acquisition system. For example, in the nuclear magnetic resonance image acquisition system, the image acquisition unit 505 is embedded in a nuclear magnetic resonance instrument bed of the nuclear magnetic resonance image acquisition system, and the processor 501, the memory 502, the power supply 503, and the input unit 504 are embedded in a console.

For specific implementations of the above operations, refer to the foregoing embodiments. Details are not described herein again.

It may be learned from above that, in the image region localization apparatus in this embodiment, the processor 501 is configured to acquire a plurality of 3D images of a target part; and extract image features of the plurality of 3D images. Then the processor 501 is configured to fuse the image features of the plurality of 3D images to obtain fused features. The processor 501 is configured to determine voxel types corresponding to voxels in the 3D images according to the fused features; select, from the 3D images, target voxels of which the voxel type is a preset voxel type to obtain position information of the target voxels; and localize a target region based on the position information of the target voxels. According to the solution, the processor 501 may extract different image features provided by the 3D images of different modalities, obtain fused features including multi-modality information according to the image features, and directly localize the region according to the fused features. Therefore, the solution can reduce the probability of a false determination, thereby improving a localizing accuracy for target regions.

A person of ordinary skill in the art may understand that, all or some steps of the methods in the foregoing embodiments may be implemented by using instructions, or implemented through instructions controlling relevant hardware, and the instructions may be stored in a computer-readable memory and loaded and executed by a processor.

Accordingly, an embodiment of this application provides a memory, storing a plurality of instructions. The instructions can be loaded by the processor, to perform the steps in any image region localizing method according to the embodiments of this application. For example, the instructions may perform the following steps:

acquiring a plurality of 3D images of a target part, the plurality of 3D images including a plurality of 3D images of different modalities;

extracting image features of the plurality of 3D images.

fusing the image features of the plurality of 3D images to obtain fused features.

determining voxel types corresponding to voxels in the 3D images according to the fused features;

selecting, from the 3D images, target voxels of which the voxel type is a preset voxel type to obtain position information of the target voxels; and localizing a target region based on the position information of the target voxels.

The memory may include: a read-only memory (ROM), a random access memory (RAM), a magnetic disk, an optical disc or the like.

Because the instructions stored in the memory may perform the steps of any image region localization method provided in the embodiments of this application, the instructions can implement beneficial effects that can be implemented by any image region localization method provided in the embodiments of this application. For details, reference may be made to the foregoing embodiments. Details are not described herein again.

The image region localization method and apparatus and the medical image processing device provided in the embodiments of this application are described above in detail. Although the principles and implementations of this application are described by using specific examples in this specification, the descriptions of the foregoing embodiments are merely intended to help understand the method and the core idea of the method of this application. Meanwhile, a person skilled in the art may make modifications to the specific implementations and application range according to the idea of this application. In conclusion, the content of this specification is not to be construed as a limitation to this application.

As used herein, the term "unit" or "module" refers to a computer program or part of the computer program that has a predefined function and works together with other related parts to achieve a predefined goal and may be all or partially implemented by using software, hardware (e.g., processing circuitry and/or memory configured to perform the predefined functions), or a combination thereof. Each unit or module can be implemented using one or more processors (or processors and memory). Likewise, a processor (or processors and memory) can be used to implement one or more modules or units. Moreover, each module or unit can be part of an overall module that includes the functionalities of the module or unit. The division of the foregoing functional modules is merely used as an example for description when the systems, devices, and apparatus provided in the foregoing embodiments performs image region localization and/or medical image processing. In practical application, the foregoing functions may be allocated to and completed by different functional modules according to requirements, that is, an inner structure of a device is divided into different functional modules to implement all or a part of the functions described above.

What is claimed is:

1. An image region localization method, comprising:
    acquiring a plurality of three-dimensional (3D) images of a target body part of a patient, the plurality of 3D images including a first 3D image set having a first magnetic resonant imaging (MRI) modality of a plurality of MRI modalities and a second 3D image set having a second MRI modality of the plurality of MRI modalities, wherein the first MRI modality is different from the second MRI modality and the plurality of MRI modalities are selected from the group consisting of Magnetic Resonance Angiography (MRA), diffusion weighted image (DWI), apparent diffusion coefficient (ADC), fat suppression (FS) imaging, and dynamic contrast-enhanced (DCE) imaging;
    registering the first 3D image set having the first MRI modality with the second 3D image set having the second MRI modality so that images in the first 3D image set and images in the second 3D image set have the same image dimensions and the same coordinate system;
    after the registering, extracting first image features from the first 3D image set having the first MRI modality and extracting second image features from the second 3D image set having the second MRI modality, wherein the first image features and the second image features are different image features;
    fusing the extracted first and second image features to obtain fused features having multi-modality information based on the extracted first and second image features;
    determining voxel types corresponding to voxels in the 3D images according to the fused features, each voxel type corresponding to a respective pathological type;
    selecting, from the 3D images, target voxels having a preset voxel type corresponding to a predefined pathological type;
    obtaining position information of the target voxels; and
    localizing a target region within the target body part based on the position information of the target voxels.

2. The method according to claim 1, wherein determining the voxel types further comprises:
    for each of the voxels in the 3D images:
        determining a respective fused feature corresponding the voxel;
        calculating a fused feature probability corresponding to the respective fused feature;
        determining a probability that the voxel corresponds to a respective voxel type of the voxel types based on the calculated fused feature probability; and
        determining the preset voxel type to which the voxel corresponds based on the determined probability.

3. The method according to claim 1, wherein fusing the extracted first and second image features further comprises:
    acquiring preset feature weights corresponding to the first and second image features; and
    weighting the image features of the plurality of 3D images based on the preset feature weights.

4. The method according to claim 3, wherein weighting the image features of the plurality of 3D images based on the preset feature weights further comprises:
    based on the position information of the target voxels, determining a first plurality of image features corresponding to voxels having the same position in the plurality of 3D images;
    weighting the first plurality of image features with the preset feature weights to obtain a plurality of weighted image features; and
    accumulating the plurality of weighted image features to obtain fused features of the voxels.

5. The method according to claim 1, wherein localizing the target region further comprises:
    selecting a target 3D image from the plurality of 3D images; and
    localizing the target region on the target 3D image based on the position information of the target voxels.

6. The method according to claim 5, wherein localizing the target region further comprises:
    determining corresponding voxels on the target 3D image based on the position information of the target voxels to obtain the corresponding voxels; and
    setting a voxel value of each of the corresponding voxels to a preset value to identify the target region.

7. The method according to claim 5, wherein localizing the target region further comprises:
    calculating a mean of the position information of all of the target voxels to obtain position information of a central point of the target region; and
    localizing the central point of the target region on the target 3D image based on the position information of the central point.

8. The method according to claim 1, wherein extracting the image features of the plurality of 3D images comprises:
    preprocessing the plurality of 3D images to obtain a plurality of preprocessed 3D images; and
    extracting image features of the plurality of preprocessed 3D images.

9. The method according to claim 8, wherein preprocessing the plurality of 3D images further comprises:
    acquiring a reference coordinate system and original coordinate systems of the plurality of 3D images; and
    transforming the original coordinate systems of the plurality of 3D images into the reference coordinate system.

10. The method according to claim 8, wherein preprocessing the plurality of 3D images further comprises:
acquiring a reference voxel spacing and original voxel spacings of the plurality of 3D images; and
transforming the original voxel spacings of the plurality of 3D images into the reference voxel spacing.

11. The method according to claim 8, wherein preprocessing the plurality of 3D images further comprises:
acquiring a reference dimension and original dimensions of the plurality of 3D images; and
transforming the original dimensions of the plurality of 3D images into the reference dimension.

12. A computing device, comprising:
one or more processors; and
memory storing one or more programs for execution by the one or more processors, the one or more programs comprising instructions for:
acquiring a plurality of three-dimensional (3D) images of a target body part of a patient, the plurality of 3D images including a first 3D image set having a first magnetic resonant imaging (MRI) modality of a plurality of MRI modalities and a second 3D image set having a second MRI modality of the plurality of MRI modalities, wherein the first MRI modality is different from the second MRI modality and the plurality of MRI modalities are selected from the group consisting of, Magnetic Resonance Angiography (MRA), diffusion weighted image (DWI), apparent diffusion coefficient (ADC), fat suppression (FS) imaging, and dynamic contrast-enhanced (DCE) imaging;
registering the first 3D image set having the first MRI modality with the second 3D image set having the second MRI modality so that images in the first 3D image set and images in the second 3D image set have the same image dimensions and the same coordinate system;
after the registering, extracting first image features from the first 3D image set having the first MRI modality and extracting second image features from the second 3D image set having the second MRI modality, wherein the first image features and the second image features are different image features;
fusing the extracted first and second image features to obtain fused features having multi-modality information based on the extracted first and second image features;
determining voxel types corresponding to voxels in the 3D images according to the fused features, each voxel type corresponding to a respective pathological type;
selecting, from the 3D images, target voxels having a preset voxel type corresponding to a predefined pathological type;
obtaining position information of the target voxels; and
localizing a target region within the target body part based on the position information of the target voxels.

13. The computing device according to claim 12, wherein the instructions for determining the voxel types further comprise instructions for:
for each of the voxels in the 3D images:
determining a respective fused feature corresponding the voxel;
calculating a fused feature probability corresponding to the respective fused feature;
calculating a probability that the voxel corresponds to a respective voxel type of the voxel types based on the calculated fused feature probability; and
determining the preset voxel type to which the voxel corresponds based on the calculated probability.

14. The computing device according to claim 12, wherein the instructions for fusing the extracted first and second image features further comprise instructions for:
acquiring preset feature weights corresponding to the first and second image features; and
weighting the image features of the plurality of 3D images based on the preset feature weights.

15. The computing device according to claim 14, wherein the instructions for weighting the image features of the plurality of 3D images based on the preset feature weights further comprise instructions for:
based on the position information of the target voxels, determining a first plurality of image features corresponding to voxels having the same position in the plurality of 3D images;
weighting the first plurality of image features with the preset feature weights to obtain a plurality of weighted image features; and
accumulating the plurality of weighted image features to obtain fused features of the voxels.

16. The computing device according to claim 12, wherein the instructions for localizing the target region further comprise instructions for:
selecting a target 3D image from the plurality of 3D images; and
localizing the target region on the target 3D image based on the position information of the target voxels.

17. A non-transitory computer-readable storage medium storing instructions that, when executed by one or more processors of a computing device, cause the one or more processors to perform operations comprising:
acquiring a plurality of three-dimensional (3D) images of a target body part of a patient, the plurality of 3D images including a first 3D image set having a first magnetic resonant imaging (MRI) modality of a plurality of MRI modalities and a second 3D image set having a second MRI modality of the plurality of MRI modalities, wherein the first MRI modality is different from the second MRI modality and the plurality of MRI modalities are selected from the group consisting of TI Weighted MRI, T2 Weighted MRI, Magnetic Resonance Angiography (MRA), diffusion weighted image (DWI), apparent diffusion coefficient (ADC), fat suppression (FS) imaging, and dynamic contrast-enhanced (DCE) imaging;
registering the first 3D image set having the first MRI modality with the second 3D image set having the second MRI modality so that images in the first 3D image set and images in the second 3D image set have the same image dimensions and the same coordinate system;
after the registering, extracting first image features from the first 3D image set having the first MRI modality and extracting second image features from the second 3D image set having the second MRI modality, wherein the first image features and the second image features are different image features;
fusing the extracted first and second image features of the plurality of 3D images to obtain fused features having multi-modality information based on the extracted first and second image features;

determining voxel types corresponding to voxels in the 3D images according to the fused features, each voxel type corresponding to a respective pathological type;

selecting, from the 3D images, target voxels having a preset voxel type corresponding to a predefined pathological type;

obtaining position information of the target voxels; and localizing a target region within the target body part based on the position information of the target voxels.

18. The non-transitory computer-readable storage medium according to claim 17, wherein the localizing the target region further comprises:

selecting a target 3D image from the plurality of 3D images; and localizing the target region on the target 3D image based on the position information of the target voxels.

19. The non-transitory computer-readable storage medium according to claim 18, wherein localizing the target region further comprises:

determining corresponding voxels on the target 3D image based on the position information of the target voxels to obtain the corresponding voxels; and setting a voxel value of each of the corresponding voxels to a preset value to identify the target region.

20. The non-transitory computer-readable storage medium according to claim 18, wherein localizing the target region further comprises:

calculating a mean of the position information of all of the target voxels to obtain position information of a central point of the target region; and localizing the central point of the target region on the target 3D image based on the position information of the central point.

* * * * *